United States Patent [19]

Breuer et al.

[11] Patent Number: 4,587,047
[45] Date of Patent: May 6, 1986

[54] 2-OXO-1-[[(SUBSTITUTED SULFONYL)AMINO]-CARBONYL]AZETIDINES

[75] Inventors: Hermann Breuer, Schoenhofen, Fed. Rep. of Germany; William A. Slusarchyk, Belle Mead, N.J.; Theodor Denzel; Uwe D. Treuner, both of Regensburg, Fed. Rep. of Germany

[73] Assignee: E. R. Squibb & Sons, Inc., Princeton, N.J.

[21] Appl. No.: 364,352

[22] Filed: Apr. 1, 1982

Related U.S. Application Data

[63] Continuation-in-part of Ser. No. 252,672, Apr. 9, 1981, abandoned.

[51] Int. Cl.⁴ .................. C07D 205/08; C07D 403/12; C07D 401/12; A61K 31/395
[52] U.S. Cl. .................. 260/239 A; 260/239.3 R; 544/333; 544/334; 260/243.3; 544/359; 544/364; 260/244.4; 544/366; 544/369; 260/245.4; 544/370; 544/371; 260/245.5; 544/372; 544/367; 260/245.6; 544/374; 544/379; 260/245.7; 546/187; 546/193; 260/330.3; 546/194; 546/207; 260/330.4; 546/209; 546/210; 544/182; 546/211; 546/212; 544/215; 546/213; 546/256; 544/279; 546/275; 546/276; 544/295; 546/278; 546/279; 544/296; 546/280; 546/281; 544/300; 546/283; 546/284; 544/301; 544/310; 544/311; 544/312; 544/316; 544/317; 544/319; 544/320; 544/321; 544/322; 544/323; 544/324; 544/325; 544/326; 544/327; 544/331; 544/332

[58] Field of Search ......... 260/239 A, 245.4, 239.3 R, 260/243.3, 244.4, 245.5, 245.6, 245.7, 330.3, 330.9; 544/182, 215, 279, 295, 296, 300, 301, 310-312, 316, 317, 319-327, 331-334, 359, 364, 366, 369-372, 367, 374, 379; 546/187, 193, 194, 207-213, 256, 275, 276, 278-281, 283, 284

[56] References Cited

PUBLICATIONS

Aue et al., J. Org. Chem. 40, 2356 (1975).
Weyer et al., Chem. Abs. 95, 168964c (1981).

Primary Examiner—Mark L. Berch
Attorney, Agent, or Firm—Lawrence S. Levinson; Donald J. Barrack

[57] ABSTRACT

Antibacterial activity is exhibited by β-lactams having a

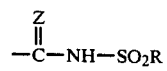

substituent in the 1-position and an acylamino substituent in the 3-position wherein Z is oxygen or sulfur, and R is alkyl, alkenyl, alkynyl, substituted alkyl, phenyl, substituted phenyl, a 5,6 or 7-membered heterocycle ($R_c$), phenylalkyl, (substituted phenyl)alkyl, $R_c$-alkyl or —$NR_aR_b$ wherein $R_a$ and $R_b$ are the same or different and each is hydrogen, alkyl, substituted alkyl, phenyl, substituted phenyl, phenylalkyl, or (substituted phenyl)alkyl or one of $R_a$ and $R_b$ is hydrogen, alkyl, phenyl, substituted phenyl, phenylalkyl or (substituted phenyl)alkyl and the other is amino, alkanoylamino, arylcarbonylamino, alkoxycarbonylamino, alkylsulfonylamino, alkylamino, dialkylamino, phenylamino, (substituted phenyl)amino, hydroxy, cyano, alkoxy, phenyloxy, (substituted phenyl)oxy, phenylalkoxy, (substituted phenyl)alkoxy, $R_c$, $R_c$-alkyl, $R_c$-alkoxy, alkylsulfonyl, alkylmethyleneamino, phenylmethyleneamino or (substituted phenyl)methyleneamino.

42 Claims, No Drawings

2-OXO-1-[[(SUBSTITUTED SULFONYL)AMINO]-CARBONYL]AZETIDINES

This is a continuation-in-part of U.S. patent application Ser. No. 252,672, filed Apr. 9, 1981, and now abandoned.

RELATED APPLICATIONS

U.S. patent application Ser. No. 226,562, filed Jan. 19, 1981, discloses β-lactam antibiotics having a sulfonic acid salt (—SO₃⊖M⊕; M⊕ is a cation) in the 1-position and an acylamino substituent in the 3-position.

U.S. patent application Ser. No. 202,830, filed Oct. 31, 1980, now U.S. Pat. No. 4,337,197 issued June 29, 1982, discloses β-lactam antibiotics having a sulfate (—O—SO₃⊖M⊕; M⊕ is a cation) substituent in the 1-position and an acylamino substituent in the 3-position.

BACKGROUND OF THE INVENTION

The β-lactam ring,

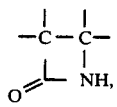

has been known since the late nineteenth century. While knowledge of β-lactam chemistry developed during the early 1900's, it was not until 1929 that Fleming reported in *Brit. J. Exper. Pathol.*, 10, 226 (1929) that a fermentation product of the organism *Penicillium notatum* had antibiotic properties. The compound which Fleming had worked with was benzylpenicillin,

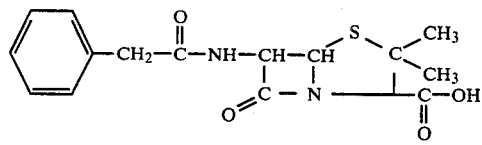

The in vivo activity of benzylpenicillin against various bacteria was reported by Chain et al. in Lancet, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid,

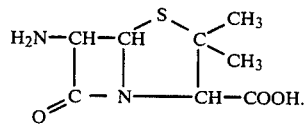

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalosporin C,

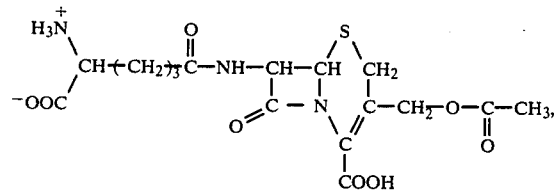

proved to be an important stepping stone in cephalosporin research. Removal of the acyl group in the 7-position of cephalosporin C yields 7-aminocephalosporanic acid,

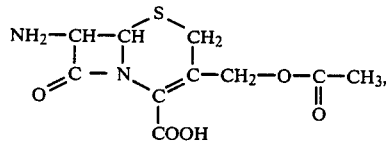

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3):122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

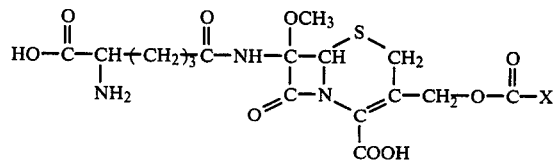

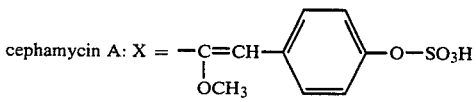
cephamycin A: X = —C=CH—⌬—O—SO₃H
             |
             OCH₃

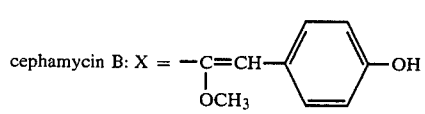
cephamycin B: X = —C=CH—⌬—OH
             |
             OCH₃

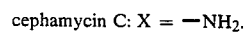
cephamycin C: X = —NH₂.

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVIII (1):1 (1975), disclose the isolation from a fermentation broth of Streptomyces species 372A of (S)-alanyl-3-[α-(S)-chloro-3-(S)-hydroxy-2-oxo-3-azetidinyl-methyl]-(S)-alanine, which has the formula

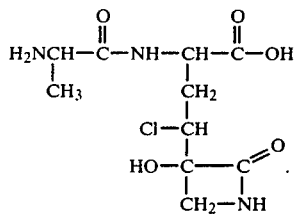

The structure of the above naturally occurring monocyclic β-lactam containing molecule is similar to the structure of the earlier discovered β-lactam containing molecules known as tabotoxins, i.e.,

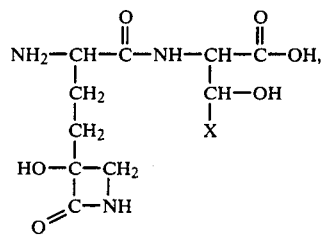

wherein X is hydrogen or methyl as reported by Stewart, *Nature*, 229:174 (1971), and Taylor et al., *Biochem. Biophys. Acta.*, 286:107 (1972).

Recently, several novel series of naturally occurring β-lactam antibiotics have been isolated. The nocardicins, noncardicin A and B, are monocyclic β-lactams having the formula

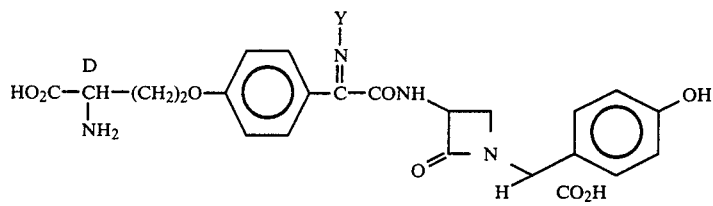

nocardicin A: Y=-syn(Z)OH
nocardicin B: Y=-anti(E)OH, as reported by Hashimoto et al., *The Journal of Antibiotics*, XXIX (9):890 (1976).

Clavulanic acid, a bicyclic β-lactam antibiotic isolated from fermentation broths of *Streptomyces clavuligerus*, has the formula

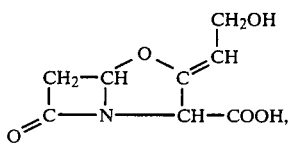

i.e., Z-(2R,5R)-3-(β-hydroxyethylidene)-7-oxo-4-oxa-1-azabicyclo[3,2,0]heptane-2-carboxylic acid, as reported by Lloyd et al., *J.C.S. Chem. Comm.*, 266 (1976).

Still another recently isolated β-lactam antibiotic is thienamycin, an antibiotic isolated from the fermentation broths of *Streptomyces cattleya*. As reported by Albers-Schonberg et al., *J.A.C.S.*, 100:20, 6491 (1978), thienamycin has the structure

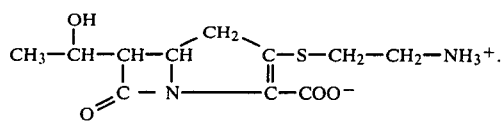

Additional fused β-lactams, olivanic acid derivatives, have recently been isolated from cultures of *Streptomyces olivaceus*. As disclosed by Brown et al., *J.C.S. Chem. Comm.*, these olivanic acid derivatives have the formulas

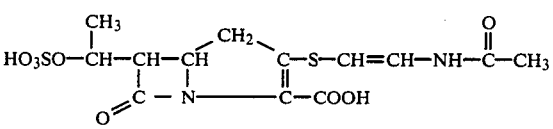

and

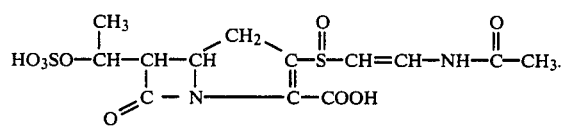

The isolation of the above antibiotics, and a discussion of their activity, is reported by Butterworth et al., *The Journal of Antibiotics*, XXXII (4):294 (1979) and by Hood et al., *The Journal of Antibiotics*, XXXII (4):295 (1979).

Another recently isolated β-lactam antibiotic is PS-5, reported by Okamura et al., *The Journal of Antibiotics*, XXXI: 480 (1978) and *The Journal of Antibiotics*, XXXII (4):262 (1979). The structure of this antibiotic, which is produced by *Streptomyces cremeus* subspecies auratilis, is reported to be

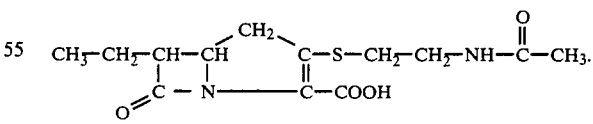

Structurally related antibiotics PS-6 and PS-7 are reported in European Patent application serial no. 1,567 to have the respective structures

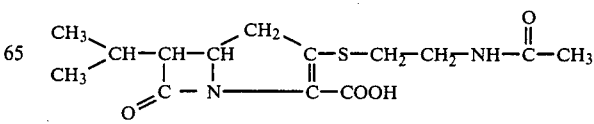

-continued
and

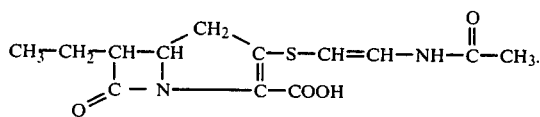

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a substituent having the formula

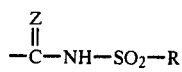

attached to the nitrogen atom in the nucleus.

β-Lactams having a

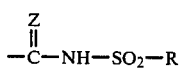

substituent in the 1-position and an acylamino substituent in the 3-position (and salts thereof) exhibit activity against a range of gram-negative and gram-positive bacteria.

Illustrative members of the novel family of β-lactam antibiotics of this invention are those encompassed by the formula

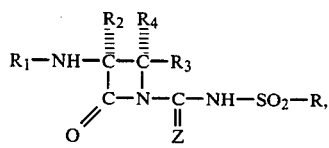

I and salts thereof.

In addition to the above described β-lactams having a

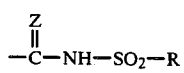

substituent in the 1-position and an acylamino substituent in the 3-position, this invention also encompasses β-lactams having a

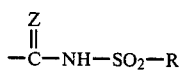

substituent in the 1-position and an amino substituent in the 3-position. Illustrative compounds of this type have the formula

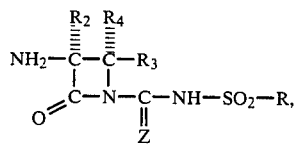

II and salts thereof. These compounds are intermediates useful for the preparation of corresponding 3-acylamino compounds.

As used in formulas I and II, and throughout the specification, the symbols are as defined below.

R is alkyl, alkenyl, alkynyl, substituted alkyl, phenyl, substituted phenyl, a 5,6 or 7-membered heterocycle (referred to hereinafter as $R_c$), phenylalkyl, (substituted phenyl)alkyl, $R_c$-alkyl or $-NR_aR_b$ wherein $R_a$ and $R_b$ are the same or different and each is hydrogen, alkyl, substituted alkyl, phenyl, substituted phenyl, phenylalkyl, or (substituted phenyl)alkyl, or one of $R_a$ and $R_b$ is hydrogen, alkyl, phenyl, substituted phenyl, phenylalkyl or (substituted phenyl)alkyl, and the other is amino ($-NH_2$), alkanoylamino, arylcarbonylamino, alkoxycarbonylamino, alkylsulfonylamino, alkylamino, dialkylamino, phenylamino, (substituted phenyl)amino, hydroxy, cyano ($-C\equiv N$), alkoxy, phenyloxy, (substituted phenyl)oxy, phenylalkoxy, (substituted phenyl)alkoxy, $R_c$, $R_c$-alkyl, $R_c$-alkoxy, alkylsulfonyl, alkylmethyleneamino, (alkyl$-CH=N-$), phenylmethyleneamino or (substituted phenyl)methyleneamino;

$R_1$ is acyl;

$R_2$ is hydrogen or methoxy;

$R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl, 2-phenylethynyl, carboxyl, $-CH_2X_1$ (wherein $X_1$ is azido, amino ($-NH_2$), hydroxy, alkanoylamino, alkylsulfonyloxy, phenylsulfonyloxy, (substituted phenyl)sulfonyloxy, phenyl, substituted phenyl, halogen, benzylthio, (substituted phenyl)methylthio, triphenylmethylthio, cyano or mercapto), $-S-X_2$ or $-O-X_2$ (wherein $X_2$ is alkyl, phenyl, substituted phenyl, alkanoyl, phenylcarbonyl, (substituted phenyl)carbonyl, or heteroarylcarbonyl), or

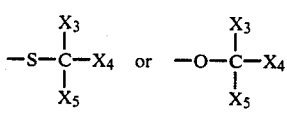

(wherein one of $X_3$ and $X_4$ is hydrogen and the other is hydrogen or alkyl, or $X_3$ and $X_4$ when taken together with the carbon atom to which they are attached form a cycloalkyl group, and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

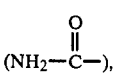

(substituted amino)carbonyl, or cyano ($-C\equiv N$)); and

Z is oxygen or sulfur.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The terms "alkanoyl", "alkenyl", "alkynyl", "alken-1-yl" and "alkyn-1-yl" refer to both straight and branched chain groups. Those groups having 2 to 10 carbon atoms are preferred.

The term "halogen" refers to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued March 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino(—NH$_2$), halogen, hydroxyl, trifluoromethyl, alkyl (of 1 to 4 carbon atoms), alkoxy (of 1 to 4 carbon atoms) or carboxyl groups.

The term "substituted alkyl" refers to alkylgroups substituted with one, or more, azido, amino (—NH$_2$), alkylamino, dialkylamino, (phenylalkyl)amino, (substituted phenylalkyl)amino, alkanoylamino, halogen, hydroxy, carboxy, cyano, alkoxycarbonyl, aminocarbonyl, alkanoyloxy, alkoxy, phenyloxy, (substituted phenyl)oxy, (heteroaryl)oxy, mercapto, alkylthio, phenylthio, (substituted phenyl)thio, alkylsulfinyl, or alkylsulfonyl groups.

The expression "a 5, 6 or 7-membered heterocycle" (referred to as "R$_c$") refers to substituted and unsubstituted, aromatic and non-aromatic groups containing one or more nitrogen, oxygen or sulfur atoms. Exemplary substituents are oxo(=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furylimino

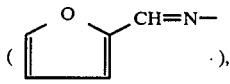

benzylimino and substituted alkyl groups (wherein the alkyl group has 1 to 4 carbons). One type of "5,6 or 7-membered heterocycle" is the "heteroaryl" group. The term "heteroaryl" refers to those 5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazoyly, triazinyl, and tetrazolyl. Exemplary nonaromatic heterocycles (i.e., fully or partially saturated heterocyclic groups are substituted and unsubstituted piperidinyl, piperazinyl, imidazolidinyl, oxazolidinyl, pyrrolidinyl, tetrahydropyrimidinyl, dihydrothiazolyl and hexahydroazepinyl. Exemplary of the substituted 5, 6 or 7-membered heterocycles are 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazopinyl, 2-oxo-3-pyrrolidinyl, 2-oxo-3-furanyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NY$_1$Y$_2$ where Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy, or amino (—NH$_2$).

The term "acyl" includes all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

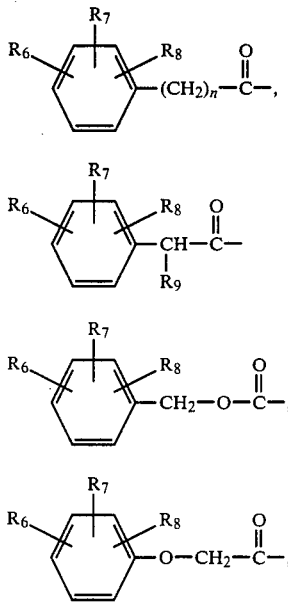

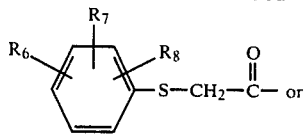

or

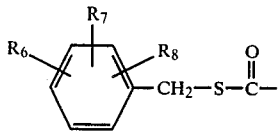

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_9$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

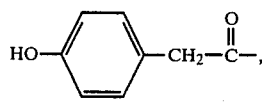

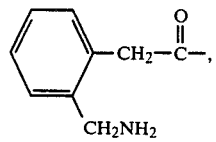

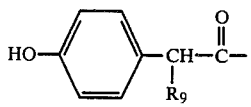

($R_9$ is preferably a carboxyl salt or sulfo salt) and

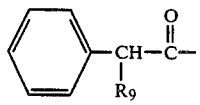

($R_9$ is preferably a carboxyl salt or sulfo salt).

(c) Heteroaromatic groups having the formula

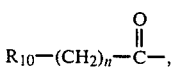

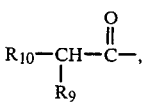

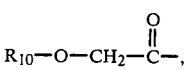

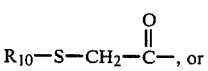

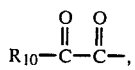

wherein n is 0, 1, 2 or 3; $R_9$ is as defined above; and $R_{10}$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms alkoxy of 1 to 4 carbon atoms, or

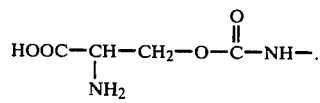

Preferred heteroaromatic acyl groups include those groups of the above formulas wherein $R_{10}$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)(carbonyl]amino]arylacetyl groups having the formula

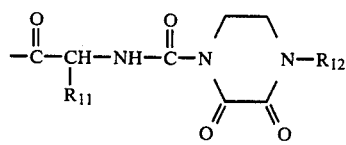

wherein $R_{11}$ is an aromatic group (including carbocyclic aromatics such as those of the formula

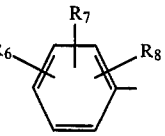

and heteroaromatics as included within the definition of $R_{10}$); and $R_{12}$ is alkyl, substituted alkyl (wherein the alkyl group is substituted with one or more halogen, cyano, nitro, amino or mercapto groups), arylmethyleneamino (i.e., —N=CH—$R_{11}$ wherein $R_{11}$ is as defined above), arylcarbonylamino (i.e.,

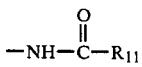

wherein $R_{11}$ is as defined above) or alkylcarbonylmino.

Preferred [[(4-substituted-2,3-dioxo-1-piperazinyl)-carbonyl]amino]arylacetyl groups include those wherein $R_{12}$ is ethyl, phenylmethyleneamino or 2-furylmethyleneamino.

(e) (Substituted oxyimino)arylacetyl groups having the formula

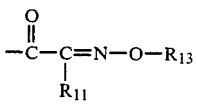

wherein $R_{11}$ is as defined above and $R_{13}$ is hydrogen, alkyl, cycloalkyl, alkylaminocarbonyl, arylaminocarbonyl (i.e.,

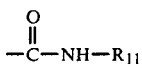

wherein $R_{11}$ is as defined above) or substituted alkyl (wherein the alkyl groups is substituted with 1 or more halogen, cyano, nitro, amino, mercapto, alkylthio, aromatic group (as defined by $R_{11}$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy (phenylmethoxy)phosphinyl, or dialkoxyphosphinyl substituents).

Preferred (substituted oxyimino)arylacetyl groups include those wherein $R_{11}$ is 2-amino-4-thiazolyl. Also preferred are those groups wherein $R_{13}$ is methyl, ethyl, carboxymethyl, 1-carboxy-1-methylethyl or 2,2,2-trifluoroethyl.

(f) (Acylamino)arylacetyl groups having the formula

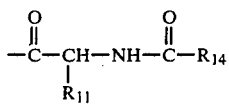

wherein $R_{11}$ is as defined above and $R_{14}$ is

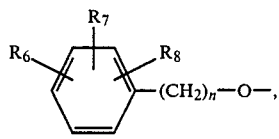

amino, alkylamino, (cyanoalkyl)amino, amido, alkylamido, (cyanoalkyl)amido,

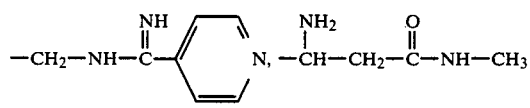

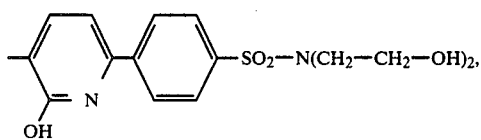

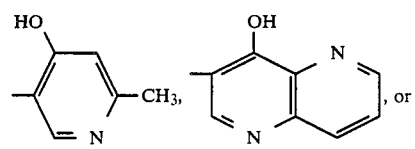

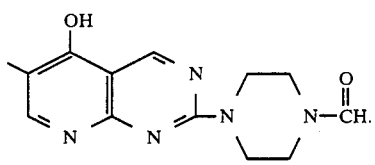

Preferred (acylamino)arylacetyl groups of the above formula include those groups wherein $R_{14}$ is amino or amido. Also preferred are those groups wherein $R_{11}$ is phenyl or 2-thienyl.

(g) [[[3-Substituted-2-oxo-1-imidazolidinyl]carbonyl]amino]arylacetyl groups having the formula

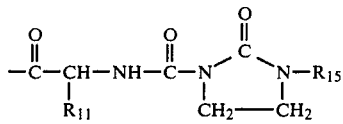

wherein $R_{11}$ is as defined above and $R_{15}$ is hydrogen, alkylsulfonyl, arylmethyleneamino (i.e., $-N=CH-R_{11}$ is as defined above),

(wherein $R_{16}$ is hydrogen, alkyl or halogen substituted alkyl), aromatic group (as defined by $R_{11}$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_{11}$ is phenyl or 2-thienyl. Also preferred are those groups wherein $R_{15}$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicylclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

β-Lactams having a

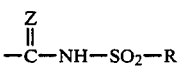

substituent in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

With respect to the preferred β-lactams of formulas I and II, the structural formulas have been drawn to show the stereochemistry at the chiral center in the 3-position.

Also included within the scope of this invention are racemic mixtures which contain the above-described β-lactams.

DETAILED DESCRIPTION OF THE INVENTION

β-Lactams having a

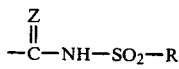

substituent in the 1-position of the β-lactam nucleus and an acylamino substituent in the 3-position of the β-lactam nucleus, and salts thereof, have activity against a range of gram-negative and gram-positive organisms. For example, the compounds of examples 4,9,12,14,17,18,19,30, 34, and 35 (infra.) are highly active against a range of aerobic gram-negative microorganisms including, for example, strains of *Escherichia coli*, Klebsiella sp., Proteus sp., Enterobacter sp., *Serratia marcescens* and *Pseudomonas aeruginosa*. The compounds show good stability to β-lactamases, for example, those enzymes produced by aerobic gram-negative organisms and classified into Groups I–V by Richmond & Sykes, "Advances in Microbial Physiology" (Rose et al., eds.), Vol. 9, 31, Academic Press, London & New York.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

A

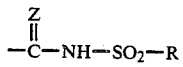

activating group can be introduced onto the nitrogen atom of a β-lactam by reacting the β-lactam with the appropriate isocyanate having the formula

O=C=N—SO₂—R    III or with the appropriate isothiocyanate having the formula

S=C=N—SO₂—R.    IIIb

The reaction is preferably run in an organic solvent, e.g., an inert solvent such as tetrahydrofuran or dimethoxyethane, in the presence of a base such as triethylamine or alkyl lithium.

An alternative, and preferred route for introducing a

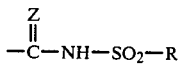

substituent onto the nitrogen atom of a β-lactam when R is an amino or substituted amino group, comprises first reacting the β-lactam with an isocyanate having the formula O=C=N—SO₂—Y    IVa or with the appropriate isothiocyanate having the formula S=C=N—SO₂—Y    IVb wherein Y is a leaving group, e.g., a halogen such as chlorine. The reaction is preferably run in an inert organic solvent, e.g., a halocarbon such as dichloromethane or in acetonitrile. The resulting intermediate has a

substituent on the nitrogen atom of the β-lactam. Displacement of the leaving group ("Y") with the desired —NR$_a$R$_b$ group can be accomplished with the appropriate nucleophile having the formula HNR$_a$R$_b$. Alternatively, the displacement of the leaving group ("Y") can be accomplished by reaction with a protected form of the compound HNR$_a$R$_b$, such as the appropriate silyl protected compound, followed by hydrolysis of the silyl group or groups.

The β-lactams of formula I wherein R₂ is hydrogen can be prepared from a 3-protected amino-2-azetidinone having the formula

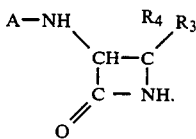

In formula V, and throughout the specification, the symbol "A" refers to an amino protecting group. These groups are well known in the field of β-lactam chemistry, and the particular group chosen is not critical. Benzyloxycarbonyl, trityl, and t-butoxycarbonyl are exemplary protecting groups.

The addition of a

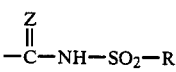

activating group to a compound of formula V (using the procedure described above) yields a compound having the formula

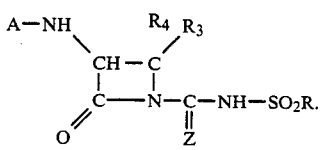

Deprotection of a compound of formula VI using conventional techniques yields the corresponding key intermediate having the formula

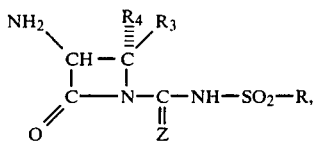 VII or a salt thereof. The particular deprotection reaction used will, of course, depend on the protecting group ("A") present. If, for example, A is a t-butoxycarbonyl protecting group, deprotection can be accomplished by treatment of a compound of formula VI with acid (e.g., formic acid or trifluoroacetic acid). If, for example, A is a benzyloxycarbonyl protecting group, deprotection can be accomplished by catalytic hydrogenation of a compound of formula VI.

Well known acylation techniques can be used to convert an intermediate of formula VII to a corresponding product of formula I. Exemplary techniques include reaction of a compound of formula VII with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such aas N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

An alternative procedure for preparing the compounds of formula I wherein $R_2$ is hydrogen comprises first acylating (acylation techniques have been described above) a 3-amino-2-azetidinone having the formula

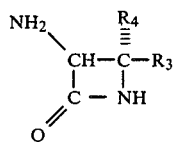 VIII to yield an intermediate having the formula

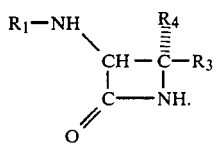 IX

A

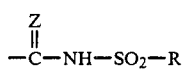

activating group can be introduced in the 1-position of a compound of formula IX (using the procedures described above) to obtain the corresponding product of formula I. In those instances wherein the acyl side-chain "$R_1$" contains reactive functionality (such as amino groups), it may be necessary to first protect those functional groups, then carry out the addition of the activating group in the 1-position, and finally deprotect the resulting product.

Still another synthesis for the preparation of compounds of formula I wherein $R_2$ is hydrogen comprises the use of a 3-azido-2-azetidinone having the formula

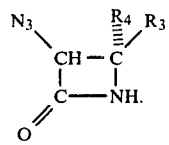 X

A

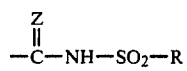

activating group can be introduced in the 1-position of a compound of formula X (using the procedures described above) to obtain the corresponding compound having the formula

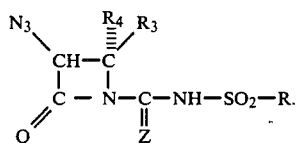 XI

The compounds of formula XI are novel intermediates, and as such, they constitute an integral part of this invention.

Reduction of an intermediate of formula XI yields the corresponding intermediate having the formula

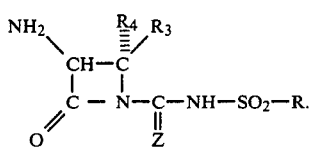 VII

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare all of the products of formula I wherein $R_2$ is hydrogen.

Alternatively, a 3-azido-2-azetidinone of formula X can be reduced to the corresponding 3-amino-2-azetidinone having the formula

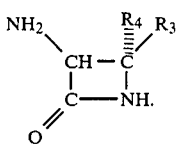 VIII

The reduction can be accomplished by catalytic (e.g., palladium on charcoal or platinum oxide) hydrogenation or with reducing agents such as zinc or triphenylphosphine. A 3-amino-2-azetidinone of formula VIII can be reacted as described above (i.e., first acylated and then treated as described above to introduce a

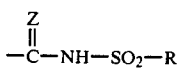

activating group in the 1-position) to yield the products of formula I wherein $R_2$ is hydrogen.

Still another synthesis for preparing the compounds of formula I wherein $R_2$, $R_3$ and $R_4$ are each hydrogen utilizes a 6-acylaminopenicillanic acid having the formula

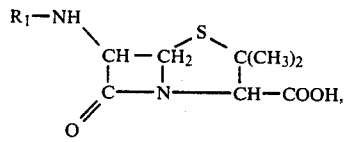

XII or a salt thereof, as the starting material. By adapting procedures described in the literature, 3-acylamino-2-azetidinone can be obtained from the corresponding 6-acylaminopenicillanic acid or formula XII: see, for example, *Chem. Soc. Special Publication* No. 28, pg. 288 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

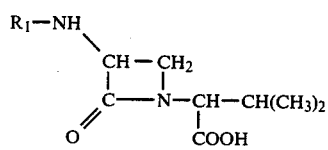

XIII by reduction using Raney nickel. The reaction can be run in water under reflux conditions.

Replacement of the carboxyl group of a compound of formula XIII with an acetate group followed by hydrolysis yields the corresponding 3-acylamino-2-azetidinone having the formula

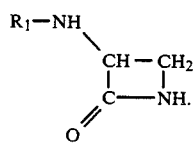

XIV

Treatment of a compound of formula XIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A

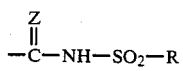

activating group can be introduced in the 1-position of a compound of formula XIV (yielding products of formula I wherein $R_2$, $R_3$ and $R_4$ are each hydrogen) using the procedures described above.

Still another variation of the abovedescribed synthetic routes for preparing a compound of formula I wherein $R_2$, $R_3$, and $R_4$ are each hydrogen comprises first desulfurizing 6-aminopenicillanic acid, acylating the resulting compound to yield a compound of formula XIII and then preceeding as described above to obtain first a 3-acylamino-2-azetidinone of formula XIV and then a product of formula I.

The azetidinones of formula I wherein $R_2$ is hydrogen and at least one of $R_3$ and $R_4$ is hydrogen can also be prepared from amino acids having the formula

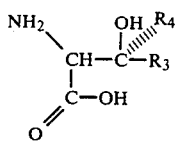

XV (at least one of $R_3$ and $R_4$ is hydrogen). The amino group is first protected (with a protecting group "A", e.g., t-butoxycarbonyl). The carboxyl group of the protected amino acid is then reacted with an amine having the formula

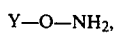

Y—O—NH$_2$, XVI wherein Y is alkyl or benzyl, in the presence of a carbodiimide to yield a compound having the formula

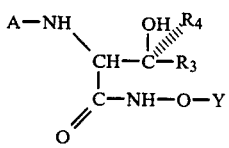

XVII

(at least one of $R_3$ and $R_4$ is hydrogen). The hydroxyl group of a compound of formula XVII is converted to a leaving group with a classical reagent, e.g., methanesulfonyl chloride (methanesulfonyl is referred to hereinafter as "Ms").

The fully protected compound having the formula

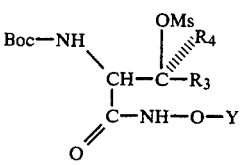

XVIII (at least one of $R_3$ and $R_4$ is hydrogen) is cyclized by treatment with base, e.g., potassium carbonate. The reaction is preferably carried out in an organic solvent such as acetone, under reflux conditions, and yields a compound having the formula

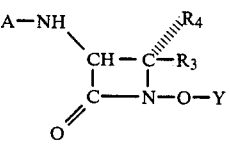

XIX (at least one of $R_3$ and $R_4$ is hydrogen).

Alternatively, cyclization of a compound of formula XVII can be accomplished without first converting the hydroxyl group to a leaving group. Treatment of a compound of formula XVII with triphenylphosphine and diethylazodicarboxylate, yields a compound of formula XIX wherein at least one of $R_3$ and $R_4$ is hydrogen.

Both of the methods disclosed above for ring closure of a compound of formula XVII result in the inversion of the stereochemistry at the carbon atom bearing the $R_3$ and $R_4$ substituents.

Removal of the protecting group from the 1-position of an azetidinone of formula XIX can be accomplished via sodium reduction when Y is alkyl, and yields an intermediate having the formula

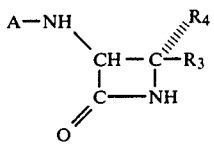   V (at least one of $R_3$ and $R_4$ is hydrogen). If Y is benzyl, catalytic (e.g., palladium on charcoal) hydrogenation will initially yield the corresponding N-hydroxy compound, which upon treatment with titanium trichloride yields an intermediate of formula V wherein at least one of $R_3$ and $R_4$ is hydrogen.

A

activating group can be introduced in the 1-position of a compound of formula V using the procedures described above, and the resulting compound can be deprotected and acylated.

The starting azetidinones of formulas V, VIII and X are obtainable using any one of numerous procedures.

A 3-azido-2-azetidinone of formula X can be prepared by first reacting an olefin having the formula

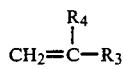   XX with a halosulfonylisocyanate (preferably chlorosulfonylisocyanate) having the formula $O=C=N-SO_2$—halogen,   XXI to yield an azetidinone having the formula

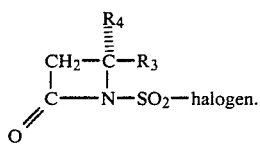   XXII

Reductive hydrolysis of an azetidinone of formula XXII yields an N-unsubstituted β-lactam having the formula

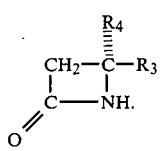   XXIII

For a more detailed description of the above described reaction sequence reference can be made to the literature; see, for example, *Chem. Soc. Rev.*, 5, 181 (1976) and *J. Org. Chem.*, 35, 2043 (1970).

An azido group can be introduced in the 3-position of an azetidinone of formula XXIII by reaction of the compound with an arylsulfonyl azide (such as toluenesulfonyl azide) to obtain a starting azetidinone having the formula

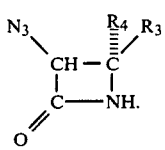   X

The reaction proceeds best by first protecting the azetidinone nitrogen with a silyl residue (e.g., t-butyldimethylsilyl, or t-butyldiphenylsilyl), then generating the anion at the 3-position of the nucleus with a strong organic base (e.g., lithium diisopropylamine) at a low temperature, and then treating the anion with toluenesulfonyl azide. The resulting intermediate is quenched with trimethylsilyl chloride, and subsequent acid hydrolysis or fluoride solvolysis of the N-protecting group yields the compound of formula X.

A 3-azido-2-azetidinone of formula X wherein $R_4$ is hydrogen can be prepared by first reacting a primary amine having the formula

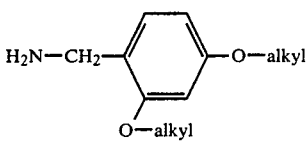   XXIVa or

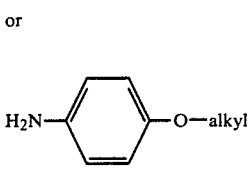   XXIVb with an aldehyde having the formula

   XXV (or a hemiacetal) to yield the corresponding Schiff base. A [2+2] cycloaddition reaction of the Schiff base with an activated form of α-azidoacetic acid yields a 3-azido-2-azetidinone having the formula

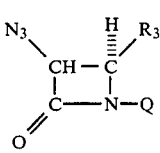   XXVI wherein Q is

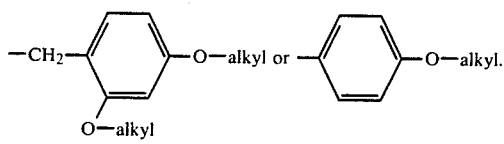

Oxidative removal of the 1-substituent yields the corresponding compound having the formula

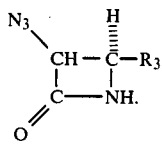   XXVII

A compound of formula V wherein $R_4$ is hydrogen can be obtained using a procedure analogous to that described above for the preparation of a 3-azido-2-azetidinone of formula X wherein $R_4$ is hydrogen. In place of an activated form of α-azidoacetic acid, an activated form of α-phthalimidoacetic acid is used, yielding a compound having the formula

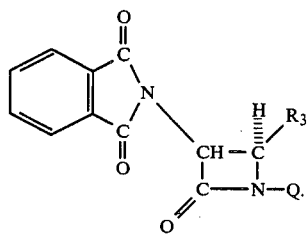   XXVIII

Reaction of a compound of formula XXVIII with a reagent such as methyl hydrazine (to cleave the phthaloyl group), followed by the introduction of a protecting group on the 3-nitrogen substituent, and oxidative removal of the 1-protecting group will yield a compound of formula V wherein $R_4$ is hydrogen.

An alternative procedure for preparing a compound of formula V, wherein one of $R_3$ and $R_4$ is hydrogen, and the other is alken-1-yl, alkyn-1-yl, 2-phenylethenyl or 2-phenylethynyl, utilizes a starting material having the formula

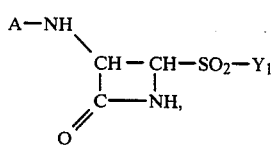   XXIX (triphenylmethyl is the preferred "A" group) and $Y_1$ is alkyl or phenyl. Reaction of a compound of formula XXIX with 1 equivalent of a methyl Grignard reagent followed by slightly more than 1 equivalent of the appropriate Grignard reagent having the formula halo—Mg—$Y_2$,   XXX wherein $Y_2$ is alkyl, alken-1-yl, alkyn-1-yl, 2-phenylethenyl or 2-phenylethynyl, yields a compound having the formula

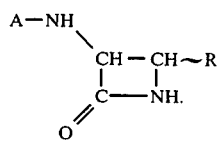   XXXI

The 3-protected amino-2-azetidinones of formula V can be obtained by first reducing a 3-azido-2-azetidinone of formula X to obtain the corresponding 3-amino-2-azetidinone (formula VIII) and then introducing the amino protecting group.

The β-lactams of formula I wherein $R_2$ is alkoxy and Z is oxygen can be prepared from the corresponding compound of formula I wherein $R_2$ is hydrogen. Halogenation of the amide nitrogen of a non-alkoxylated compound of formula I wherein Z is oxygen yields an intermediate having the formula

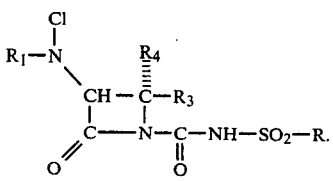   XXXII

Reagents and procedures for N-chlorinating amides are known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of an intermediate of formula XXXII with an alkoxylating agent, e.g., an alkali metal alkoxide yields a product of formula I wherein $R_2$ is alkoxy and Z is oxygen, in combination with its enantiomer. The reaction can be run in an organic solvent, e.g., a polar organic solvent such as dimethylformamide, at a reduced temperature.

Compounds of formula I wherein Z is oxygen or sulfur and $R_2$ is alkoxy can be prepared by first alkoxylating an intermediate of formula IX wherein $R_1NH$ is a carbamate (e.g., $R_1$ is benzyloxycarbonyl) and then introducing a

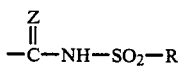

group in the 1-position of the resulting compound. Chlorination of a compound of formula IX using the procedure described above (for chlorination of a non-alkoxylated compound of formula I to yield a compound of formula XXXII) yields an intermediate having the formula

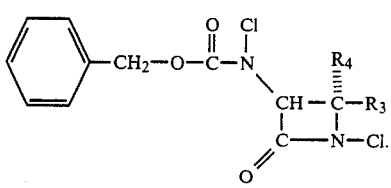   XXXIII

By using the alkoxylation procedure described above (for converting a compound of formula XXXII to a product of formula I), and subsequently adding a reducing agent such as trimethylphosphite, the compound of formula XXXIII can be converted to an intermediate having the formula

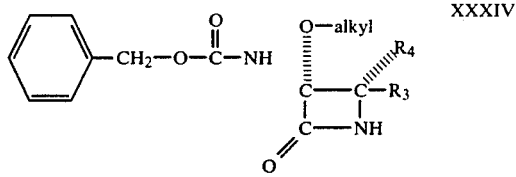

in combination with its enantiomer when $R_3$ and $R_4$ are the same. When $R_3$ and $R_4$ are different, two diastereomeric products can be formed. A

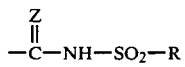

activating group can be introduced in the 1-position of a compound of formula XXXIV using the procedures described above.

Still another synthesis for preparing the products of formula I wherein $R_2$ is alkoxy comprises the initial preparation of a key intermediate having the formula

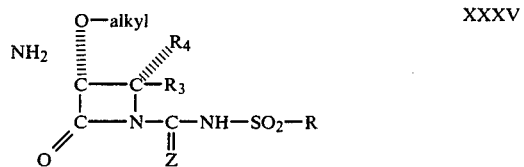

or an intermediate of formula XXXV in combination with its enantiomer. Such an intermediate can be obtained by reduction of a corresponding product of formula I wherein $R_1$ is benzyloxycarbonyl using catalytic (e.g., palladium on charcoal) hydrogenation. Acylation of an intermediate of formula XXXV yields the various products of formula I wherein $R_2$ is alkoxy.

The above procedures yield those products of formula I wherein $R_2$ is alkoxy, as a racemic mixture when $R_3$ and $R_4$ are the same. If desired the enantiomer having the R configuration can be isolated from the racemic mixture using conventional techniques such as fractional crystallization of a suitable salt with an optically active organic amine or by ion-paired chromatography utilizing an optically active cation.

Still another synthesis for preparing the products of formula I wherein $R_2$ is alkoxy and $R_3$ and $R_4$ are hydrogen comprises the preparation of a β-lactam intermediate having the formula

An intermediate of formula XXXVI can be obtained by first desulfurizing the corresponding 6-acylamino-6-alkoxypenicillanic acid or 7-acylamino-7-alkoxycephalosporanic acid by reduction using Raney nickel. The reaction can be run in water under reflux conditions; the resulting compound has the structural formula

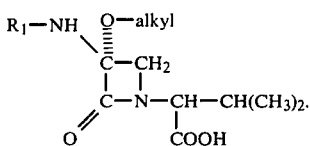

Replacement of the carboxyl group of the compound of formula XXXVII with an acetate group followed by hydrolysis yields a 3-acylamino-3-alkoxy-2-azetidinone of formula XXXVI. Treatment of a compound of formula XXXVII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

Introduction of a

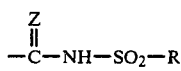

activating group in the 1-position of a compound of formula XXXVI can be accomplished using the procedures described above.

The above-described synthetic procedures for the production of the compounds of this invention have been illustrated with specific reference to the preparation of the products of formula I. As will be recognized by the practitioner of this invention, the processes have broader applicability and can be used to prepare other compounds falling within the scope of this invention; i.e., β-lactams having a

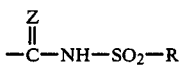

activating group in the 1-position of the β-lactam nucleus, an amino (—NH₂) or acylamino substituent in the 3-position of the β-lactam nucleus, and various substituents in the 4-position of the β-lactam nucleus.

The following examples are specific embodiments of this invention.

EXAMPLE 1

(S)-[1-[[[(4-Methylphenyl)sulfonyl]amino]carbonyl]-2-oxo-3-azetidinyl]carbamic acid, phenylmethyl ester (A) 1-[(1R)-Carboxy-2-methyl(propyl)]-2-oxo-(3S)-[[(phenylmethoxy)carbonyl]amino]azetidine A slurry of 6-aminopenicillanic acid (12.98 g) in 140 ml of water containing 5.18 g of sodium bicarbonate (stirred for about 10 minutes without complete solution) was added in one portion to a well-stirred (mechanical stirrer) suspension of Raney nickel (washed with water to pH 8.0, 260 ml of slurry=130 g) in a 70° C. oil bath. After 15 minutes the slurry was cooled, filtered, and the filtrate treated with 5.18 g of sodium bicarbonate and a solution of 11.94 g of benzyl chloroformate in 12 ml of acetone. After 30 minutes, the solution was acidified to pH 2.5 and extracted with methylene chloride. The organic layer was dried, evaporated, and triturated with etherhexane to give a total of 6.83 g of the title compound.

(B) 1-[(Acetyloxy)-2-methyl(propyl)]-2-oxo-(3S)-[[(phenylmethoxy)carbonyl]amino]azetidine A solution of 6.83 g of 1-[(1R)-carboxy-2-methyl(propyl)]-2-oxo-(3S)-[[(phenylmethoxy)-carbonyl]amino]azetidine in 213 ml of acetonitrile was treated with 1.95 g of cupric acetate monohydrate and 9.5 g of lead tetraacetate. The slurry was immersed in a 65° C. oil bath and stirred with a stream of nitrogen bubbling through the slurry until the starting material was consumed. The slurry was filtered and the solids washed with ethyl acetate. The combined filtrate and washings were evaporated in vacuo and the residue taken up in 100 ml each of ethyl acetate and water and adjusted to pH 7. The ethyl acetate layer was separated, dried, and evaporated to give 6.235 g of the title compound.

(C) (S)-(2-Oxo-3-azetidinyl)carbamic acid, phenylmethyl ester

A solution of 3.12 g of 1-[(acetyloxy)-2-methyl(propyl)]-2-oxo-(3S)-[[(phenylmethoxy)-carbonyl]amino]azetidine in 70 ml of methanol and 7 ml of water was cooled to −15° C. and 1.33 g of potassium carbonate and 349 mg of sodium borohydride was added. The reaction mixture was stirred at −15° C. -0° C. After the reaction was complete (about 2 hours), the mixture was neutralized to pH 7 with 2N HCl and concentrated in vacuo. The concentrate was adjusted to pH 5.8, saturated with salt and extracted with ethyl acetate (3 times). The organic layer was dried and evaporated in vacuo. The residue was combined with material from a similar experiment and triturated with ether to give 3.30 g of the title compound.

(D) (S)-[1-[[[(4-Methylphenyl)sulfonyl]amino]-carbonyl]-2-oxo-3-azetidinyl]carbamic acid, phenylmethyl ester, triethylammonium salt (S)-(2-Oxo-3-azetidinyl)carbamic acid, phenylmethyl ester (220 mgs) was dissolved in dry tetrahydrofuran (10 ml) and stirred well under nitrogen. Triethylamine (139 μl) was added, followed by p-toluenesulfonyl isocyanate (153 μl, 1 mmol). After 2 to 3 hours of stirring a crystalline material starts to precipitate out. After 2 hours of further stirring, the solid was removed by filtration, washed with a small volume of acetonitrile and dried in vacuo. Yield of the triethylamine salt is 332 mg, melting point 128°–130° C.

(E) (S)-[1-[[[Z(4-Methylphenyl)sulfonyl]amino-carbonyl]-2-oxo-axetidinyl]carbamic acid, phenylmethyl ester The triethylamine salt above (345 mg) was dissolved in water (15 ml) and layered with ethyl acetate (15 ml). The mixture was acidified to pH 2.0 and well shaken. The extraction with ethyl acetate was repeated twice. The combined ethyl acetate layers were dried over anhydrous sodium sulfate and evaporated to dryness in vacuo to yield 263 mg of a gum. This was crystallized from dichloromethane/hexane yielding 131 mg of product, melting point 178°–180° C.

Analysis for $C_{19}H_{19}O_6N_3S$: Calc'd: C, 54.67; H. 4.59 N, 10.07; S, 7.68. Found: C, 54.49; H, 4.71; N, 10.05; S, 7.75.

EXAMPLE 2

(S)-1-[[[(4-Methylphenyl)sulfonyl]amino]carbonyl]-2-oxo-3-aminoazetidine,triethylammonium salt (S)-[1-[[[(4-Methylphenyl)sulfonyl]amino]-carbonyl]-2-oxo-3-azetidinyl]carbamic acid, phenylmethyl ester, triethylammonium salt (150 mg; see example 1) was dissolved in dry methanol (10 ml). 10% Palladium on carbon (75 mg) was added and the mixture was hydrogenated for 30 minutes. The catalyst was removed by filtration and the filtrate was evaporated in vacuo to dryness, yielding 81 mg of the title compound.

EXAMPLE 3

(S)-N-[(4-Methylphenyl)sulfonyl]-2-oxo-3-[(phenylacetyl)amino]-1-azetidinecarboxamide (S)-1-[[[(4-Methylphenyl)sulfonyl]amino]-carbonyl]-2oxo-3-aminoazetidine, triethylammonium salt (626 mg, see example 2) was dissolved in dry acetonitrile (25 ml) and stirred under nitrogen in an ice bath. Triethylamine (0.57 ml) was added, followed by phenylacetyl chloride (0.324 ml). After 3 hours an equal volume of water was added, the pH was adjusted to 7.5, and the acetonitrile was removed in vacuo. The aqueous residue was extracted twice with ethyl acetate to remove neutral material. The aqueous layer was then acidified to pH 2.0 and extracted three times with ethyl acetate. The acidic extract was dried over anhydrous sodium sulfate and evaporated to dryness in vacuo, yielding 544 mg. This crude product, and an additional 481 mg of crude product from two other runs were combined and purified by chromatography on a column of SilicAR CC-4 (100 g), using dichloromethane and dichloromethane:methanol, 99:1 as eluants. The amorphous product was crystallized from acetonitrile to give 154 mg of crystalline material, melting point 170°–172° C.

Analysis for $C_{19}H_{19}N_3O_5S$: C, 56.85, H, 4.77; N, 10.47; S, 7.99. Found: C, 56.70; H, 4.91; N, 10.41; S, 8.05.

EXAMPLE 4

[3S(Z)]-3-[[(2-Amino-4-thiazolyl)(methoxyimino)-acetyl]amino]-N-[(4-methylphenyl)sulfonyl)-2-oxo-1-azetidinecarboxamide (A) (S)-3-Amino-2-azetidinone (S)-(2-Oxo-3-azetidinyl)carbamic acid, phenylmethyl ester (3 g; see example 1C) was hydrogenated in 100 ml of methanol in the presence of 1 g of palladium on charcoal catalyst. When the theoretical amount of hydrogen was absorbed, the catalyst was filtered off and the filtrate evaporated to dryness. On standing, 1.1 g of the title compound crystallized.

(B)[3S(Z)]-3-[[[2-(Triphenylmethylamino)-4-thiazolyl]-[methoxyimino]acetyl]amino]-2-oxoazetidine (Z)-2-(Triphenylmethylamino)-α-(methoxyimino)-4-thiazoleacetic acid (2.50 g) was dissolved in dry dimethylformamide (25 ml). 1-Hydroxybenzotriazole (863 mg, 5.64 mmol), N,N'-dicyclohexylcarbodiimide (1.164 g) and 3-amino-2-oxoazetidine (485 mg) was added sequentially, and the mixture was stirred at room temperature under dry nitrogen for 5 hours. The reaction mixture was worked up by diluting it with water (250 ml) adjusting to pH 7.5, and extracting (three times) with an equal volume of ethyl acetate. The combined extract was washed with water followed by saturated aqueous sodium chloride, dried over anhydrous sodium sulfate, and evaporated to dryness in vacuo. The crude product was purified by chromatography over SilicAR CC-7 silica gel, to give 2.50 g of solid. This was crystallized from chloroformhexane to yield 2.31 g of the title compound, melting point 233°–236° C.

(C) [3S(Z)-3-[[[2-(Triphenylmethylamino)-4-thiazolyl]-[methoxyimino]acetyl]amino]-N-[(4-methylphenyl)sulfonyl]-2-oxo-1-azetidine-carboxamide

[3S(Z)]-2-[[[2-Triphenylmethylamino)-4-thiazolyl]-[methoxyimino]acetyl]amino]-2-oxo-1-azetidine (270 mg) was dissolved in dry tetrahydrofuran (5 ml). Triethylamine (66 μl) was added followed by p-toluenesulfonyl isocyanate (80 μl). The mixture was stirred for 16 hours at room temperature. Following removal of the solvent in vacuo the residue was taken up in ethyl acetate/water and adjusted to pH 7.5. The extraction with ethyl acetate was repeated twice. The combined organic extracts were washed with water, dried over anhydrous sodium sulfate, and evaporated to dryness in vacuo to give 263 mg of crude product, which was purified by chromatography on SilicAR CC-4 silica gel (27 g), using dichloromethane:ethyl acetate (3:1), to give 123 mg of the title compound.

(D) [3S(Z)]-3-[[(2-Amino-4-thiazolyl)(methoxyimino)acetyl]amino]-N-[(4-methylphenyl)sulfonyl]-2-oxo-1-azetidinecarboxamide

[3S(Z)]-3-[[[2-(Triphenylmethylamino)-4-thiazolyl]-[methoxyimino]acetyl]amino]-N-[(4-methylphenyl)sulfonyl]-2-oxo-1-azetidine-carboxamide (122 mg) was dissolved in 70% aqueous formic acid (2 ml) and stirred under nitrogen at room temperature for 3 hours. After removal of the excess acid in vacuo the residue was taken up in ethyl acetate/water at pH 7.5. The organic layer was removed. The aqueous layer was acidified to pH 2.5 and extracted (five times) with ethyl acetate. The extract was dried over anhydrous sodium sulfate and evaporated to dryness in vacuo. The residue was dissolved in pure dioxane and lyophilized to yield 50 mg of the title compound as a fluffy powder, which was dried in vacuo at 50° C. for 2 hours, melting point 160° C. dec.

Analysis for $C_{17}H_{18}O_6N_6S_2$ Calc'd: C, 43.78; H, 3.89; N, 18.02; S, 13.75. Found: C, 43.38; H, 4.05; N. 15.86; S, 12.75.

EXAMPLE 5

(S)-N-(Methylsulfonyl)-2-oxo-3-[[(phenylmethoxy)-carbonyl]amino]-1-azetidinecarboxamide A stirred suspension of (S)-(2-oxo-3-azetidinyl)carbamic acid, phenylmethyl ester (2.20 g; see example 1C) in 60 ml of dry tetrahydrofuran under nitrogen was warmed using a water bath at 40° C. until solution occurs. The solution was cooled to −75° C., and 7.4 ml of 1.35 M sec-butyl lithium in cyclohexane (10 mmol) was added. After stirring for 2 minutes, (methylsulfonyl) isocyanate (about 1.20 g) was added. This reaction was stirred at −75° C. for 10 minutes and poured into 100 ml of 0.5 M pH 5.5 monobasic potassium phosphate buffer. Ethyl acetate was added, and the pH was adjusted to 7. After several extractions with ethyl acetate, the aqueous layer was covered with ethyl acetate and adjusted to pH 2. Repeated extraction with ethyl acetate gave an acidic extract, which was dried (sodium sulfate) and evaporated to a residue (2.61 g). Chromatography of this residue on 250 g of silicAR CC-4 using dichloromethane and then 1% methanol in dichloromethane provided 1.82 g of product as a residue.

EXAMPLE 6

(S)-N-(Methylsulfonyl)-2-oxo-3-amino-1-azetidinecarboxamide, hydrochloride salt

To a solution of 300 mg of (S)-N-(methylsulfonyl)-2-oxo-3-[[(phenylmethoxy)carbonyl]-amino-1-azetidinecarboxamide (see example 5) in 8 ml of dry methanol was added 150 mg of 10% palladium on charcoal. The mixture was hydrogenated at room temperature and 1 atmosphere for 30 minutes, and then 2 ml of water was added followed by dilute hydrochloric acid to adjust the pH to 1.8. The catalyst was filtered using water/methanol. Evaporation of the filtrate gave 65 mg of crude product. The catalyst was suspended in water, adjusted to pH 1.8 and stirred at room temperature for 15 minutes. Removal of the catalyst and evaporation of the filtrate provided additional crude product (124 mg).

EXAMPLE 7

(S)-N-(Methylsulfonyl)-2-oxo-3-[(phenylacetyl)-amino]-1-azetidinecarboxamide (S)-N-Methylsulfonyl)-2-oxo-3-amino-1-azetidinecarboxamide, hydrochloride salt (189 mg; see example 6) was suspended in 8 ml of dry acetonitrile and 0.54 ml of triethylamine, and stirred at room temperature under nitrogen until solution occurred (about 15 minutes). The solution was cooled to 0° to 5° C., and then phenyl acetylchloride (153 μl) was added. The reaction was stirred at room temperature for 3 hours and then poured into 10 ml of 0.5 M pH 5.5 monobasic potassium phosphate buffer. The pH was adjusted to 7 (dilute potassium hydroxide) and the solution was extracted twice with ethyl acetate. The aqueous layer was covered with fresh ethyl acetate, and the pH was adjusted to 2 (3N hydrochloric acid). Repeated extraction with ethyl acetate gave an acidic ethyl acetate extract, which was dried (sodium sulfate) and evaporated to a residue (196 mg). Chromatography of this material on 20 g of SilicAR CC-4 using ethyl acetate/dichloromethane (1:1) provides 96 mg of crystalline product after removal of solvent. Recrystallization from ethyl acetate/dichloromethane provides an analytical sample having a melting point 168°–170° C., dec.

Anal. Calc'd for $C_{13}H_{15}N_3O_5S$: C, 48,00; H, 4.65; N, 12.92; S, 9.84. Found: C, 47.82; H, 4.74; N, 12.86; S, 9.13.

EXAMPLE 8

(S)-3-Amino-N-(methylsulfonyl)-2-oxo-1-azetidinecarboxamide, inner salt (S)-N-(Methylsulfonyl)-2-oxo-3-[[(phenylmethoxy)-carbonyl]amino]-1-azetidinecarboxamide (2.20 g; see example 5) was stirred with 90 ml of methanol under nitrogen at 40° to 45° C. until solution occurs. The solutions was quickly cooled to room temperature and hydrogenated at one atmosphere in the presence of 1.1 g of 10% palladium on charcoal for twenty minutes. Water (20 ml) was added, and the pH was adjusted to 2.0 (1N hydrochloric acid). The product, which was absorbed on the catalyst, was collected by filtration, using Whatman #50 paper, and suspended in 25 ml of water. The pH was adjusted to 2.0 (1N hydrochloric acid), and the mixture was stirred for twenty-five minutes and filtered through Whatman #50 paper. Evaporation of the filtrate provided 611 mg of crystalline product, melting point 180° C., dec.

EXAMPLE 9

[3S(Z)]-3-[[(2-Amino-4-thiazolyl)(methoxyimino)-acetyl]amino]-N-(methylsulfonyl)-2-oxo-1-azetidinecarboxamide, potassium salt Triethylamine (0.47 ml) was added to a stirred suspension of (Z)-(2-amino-4-thiazolyl)-(methoxyimino)acetic acid (671 mg) and 2 μl of N-methylmorpholine in 5 ml of dry dimethylformamide at room temperature under nitrogen. The mixture was stirred for five minutes and then cooled to −25° C. Diphenyl chlorophosphate (0.69 ml) was added, and the mixture was stirred at −25° to −15° C. for forty minutes. Using a syringe, this mixture was transferred to a stirred mixture of (S)-3-amino-N-(methylsulfonyl)-2-oxo-1-azetidinecarboxamide, inner salt (608 mg; see example 8), 5 ml of dry dimethylformamide and 1.65 ml (11.8 mmol) of triethylamine at −25° C. under nitrogen. After stirring at −25° to −15° C. for three and a half hours, the reaction mixture was poured into 35 ml of 0.5 M, pH 5.5, monobasic potassium phosphate. Water and ethyl acetate was added, and the pH was adjusted to 7.2 using dilute potassium hydroxide. After extracting with ethyl acetate (three times), the aqueous layer was covered with fresh ethyl acetate and adjusted to pH 2.5 (1N hydrochloric acid). Repeated extraction with ethyl acetate gave an acidic ethyl acetate extract, which was dried (sodium sulfate), and evaporated to a residue (625 mg).

This residue was applied to a column of SilicAR CC-4 (50 g) packed in ethyl acetate/dichloromethane (1:1). Elution with this solvent and then ethyl acetate removes non-polar impurities. Elution with 3–4% methanol in ethyl acetate provided 334 mg of partially purified product (H+ form), which was taken up in 3 ml of 0.5 M pH 5.5 monobasic potassium phosphate buffer. The pH wa adjusted to 6.5 (dilute potassium hydroxide), and the solution was passed, using water, through a column of HP-20 resin (100 ml), which had been prewashed with the monobasic potassium phosphate buffer and then water. A combination of phosphomolybdic acid test ($PO_4^{-3}$) and Rydon's test locate the desired product. Evaporation of appropriate fractions provided 145 mg of desired potassium salt as a residue.

The aqueous pH 2.5 layer mentioned above, was evaporated to remove water and dimethylformamide. Water and ethyl acetate were added, and after adjusting the pH to 2.5, another acidic ethyl acetate extract was obtained and evaporated to a residue (658 mg). This material was dissolved in 4 ml of 0.5 M monobasic potassium phosphate buffer and adjusted to pH 6.5. Subsequent passage through 100 ml of HP-20 resin using water provided 54 mg of additional potassium salt was a residue. This material was combined with the 145 mg portion above and lyophilized from water to give 199 mg of the title potassium salt as a solid, melting point 205° C., dec.

Anal. Calc'd. for $C_{11}H_{13}N_6O_6S_2K.2\ H_2O$: C, 28.45; H, 3.69; N, 18.10; S, 13.78. Found: C, 28.75; H, 2.87; N, 18.09; S, 13.64.

EXAMPLE 10

[3S-[3α,4β]]-3-[[(1,1-Dimethylethoxy)carbonyl]-amino]-4-methyl-N-(methylsulfonyl)-2-oxo-1-azetidinecarboxamide (A) N-Benzyloxy-t-butoxycarbonyl-threonine amide A solution of 8.76 g of t-butoxycarbonyl threonine and the free amine from 6.4 g of O-benzylhydroxylamine HCl (ethyl acetate-sodium bicarbonate liberation) in 100 ml of tetrahydrofuran was treated with 6.12 g of N-hydroxybenzotriazole and 8.24 g of dicyclohexylcarbodiimide in 20 ml of tetrahydrofuran. The mixture was stirred under nitrogen for 26 hours, filtered, and evaporated in vacuo. The residue was chromatographed on a 300 g silica gel column (elution with chloroform and chloroform/ethyl acetate (3:1) yielding 7.2 g of compound. Crystallization from ether-hexane gave 4.18 g of the title compound.

(B) (3S-trans)-N-Benzyloxy-3-t-butoxycarbonylamino-4-methylazetidinone

A solution of 12.67 g of N-benzyloxy-t-butoxycarbonyl-threonine amide, 11.5 g of triphenylphosphine, and 6.23 ml of diethylazodicarboxylate in 380 ml of tetrahydrofuran was stirred under nitrogen for about 16 hours. The solution was evaporated and chromatographed on a 900 g silica gel column. Elution with chloroform-ethyl acetate (3:1) gave 13.69 g of compound that crystallized from ether-hexane to yield 9.18 g of the title compound.

(C) (3S-trans)-3-t-Butoxycarbonylamino-1-hydroxy-4-methylazetidinone

A solution of 9.18 g of (3S-trans)-N-benzyloxy-3-t-butoxycarbonylamino-4-methylazetidinone in 300 ml of 95% ethanol was stirred in an atmosphere of hydrogen with 1.85 g of 1% palladium on charcoal. After 141 minutes the slurry was filtered and evaporated in vacuo. The residue was recrystallized from ether-hexane to yield 5.12 g of the title compound.

(D) (3S-trans)-3-t-Butoxycarbonylamino-4-methylazetidinone

A solution of 4.98 g of (3S-trans)-3-t-butoxycarbonylamino-1-hydroxy-4-methylazetidinone in 200 ml of methanol was treated with 132 ml of 4.5 M ammonium acetate and then 66 ml of 1.5 titanium trichloride and stirred for 4.5 hours. The aqueous solution was diluted with an equal volume of 8% sodium chloride and extracted with ethyl acetate to give 3.48 g of crude product. Recrystallization from ether-hexane yielded 3.3 g of the title compound.

(E) [3S-[3α,4β]]-3-[[(1,1-Dimethylethoxy)carbonyl]amino]-4-methyl-N-(methylsulfonyl)-2-oxo-1-azetidinecarboxamide Sec-Butyl lithium (14.8 ml of 1.35 M solution in cyclohexane) was added to a stirred solution of (3S-trans)-3-t-butoxycarbonylamino-4-methylazetidinone (20 mmole) in 150 ml of dry tetrahydrofuran at −75° C. under nitrogen. After stirring for 2 minutes methylsulfonylisocyanate (2.4 ml) was added, and the solution was stirred for 25 minutes at −75° C. and poured into 200 ml of 0.5 M pH 5.5 monobasic potassium phosphate buffer. Water and ethyl acetate were added, and the pH was adjusted to 2.5 using 3N hydrochloric acid. The ethyl acetate layer and subsequent ethyl acetate extract was combined, dried(sodium sulfate), and evaporated to a residue (7.15 g), which was chromatographed on 450 g of SilicAR CC-4, using dichloromethane and then 1% methanol in dichloromethane, to give 3.67 g of desired product as a residue.

EXAMPLE 11

[3S-[3α,4β]]-3-Amino-4-methyl-N-(methylsulfonyl)-2-oxo-1-azetidinecarboxamide, trifluoroacetic acid salt

[3S-[3α,4β]]-3-[[(1,1-Dimethylethoxy-carbonyl-]amino]-4-methyl-N-(methylsulfonyl)-2-oxo-1-azetidinecarboxamide (482 mg; see example 10) was stirred with 4.5 ml of trifluoroacetic acid at 0° to 5° C.

under nitrogen for 30 minutes. The solution was evaporated in vacuo to a residue, which was evaporated from acetonitrile (four times) to give the desired salt as a residue.

EXAMPLE 12

[3S-[3α(Z),4β]]-3-[[(2-Amino-4-thiazolyl)(methoxyimino)acetyl]amino]-4-methyl-N-(methylsulfonyl)-2-oxo-1-azetidinecarboxamide, potassium salt Triethylamine (243 μl) was added to a stirred suspension of (Z)-(2-amino-4-thiazolyl) (methoxyimino)acetic acid (303 mg) in 4.5 ml of dry dimethylformamide at room temperature under nitrogen. After stirring for 2 minutes, the mixture was cooled to −25° C., and diphenyl chlorophosphate (312 μl) was added. The mixture was stirred for 50 minutes at −25° C. and added, via syringe, to a stirred solution of [3S-[3α,4β]]-3-amino-4-methyl-N-(methylsulfonyl)-2-oxo-1-azetidinecarboxamide, trifluoroacetic acid salt and 1.05 ml of triethylamine in dimethylformamide at −25° C. under nitrogen. The reaction was stirred for 2.5 hours at this temperature and poured into 18 ml of 0.5 M pH 5.5 monobasic potassium phosphate buffer. Ethyl acetate and water were added and the pH was adjusted to 7. The aqueous layer was separated and adjusted to 2.5, using 3N hydrochloric acid, and the solvents were removed in vacuo to give a residue, which was taken up in ethyl acetate and water (pH 2.5). Repeated extraction gave a combined ethyl acetate extract, which was dried (sodium sulfate), and evaporated to a residue. This residue was solubilized by addition of 5 ml of 0.5 M monobasic potassium phosphate buffer and adjusted to pH 6.5 using dilute aqueous potassium hydroxide. Chromatography on a column (120 ml) of HP-20 resin, using water as eluent gave 296 mg of the desired potassium salt. The lyophilized solid had a melting point 201° C., dec.

Anal. Calc'd for $C_{12}H_{15}N_6O_6S_2K.0.5 H_2O$: C, 31.92; H, 3.57; N, 18.61; S, 14.20. Found: C, 32.08; H, 3.62; N, 18.51; S, 14.07.

EXAMPLE 13

[3S-[3α(Z),4β]]3-[[(2-Amino-4-thiazolyl)-[[2-(diphenylmethoxy)-1,1-dimethyl-2-oxoethoxy]imino]acetyl]amino]-4-methyl-N-(methylsulfonyl)-2-oxo-1-azetidinecarboxamide

[3S-[3α,4β]]-3-Amino-4-methyl-N-(methylsulfonyl)-2-oxo-1-azetidinecarboxamide, trifluoroacetic acid salt (167 mg; see example 11) was dissolved in dry dimethylformamide (1.5 ml) and dry triethylamine (0.35 ml) and stirred at −25° C. under dry nitrogen. To this solution was added, via syringe, a solution of mixed anhydride which was prepared by sequentially adding (Z)-2-amino-α-[[2-(diphenylmethoxy)-1,1-dimethyl-2-oxoethoxy]imino]-4-thiazoleacetic acid (220 mg), dry triethylamine (126 μl) and diphenylchlorophosphate (155 μl, 0.75 mmol) to dry dimethylformamide (1.5 ml) and stirring for 50 minutes at −25° C. under nitrogen. The resulting mixture was stirred at −25° C. for 2.5 hours under dry nitrogen. It was then poured into 0.5 M pH 5.5 monobasic potassium phosphate buffer (6 ml) and evaporated to dryness in vacuo. The residue was taken up in ethyl acetate/water, acidified with dilute hydrochloric acid to pH 2.5 and extracted (three times) with ethyl acetate. The extract was washed with water, dried over anhydrous sodium sulfate, evaporated to dryness in vacuo, and purified by thin-layer chromatography on silica gel in ethyl acetate: methanol (4:1). The eluted product was taken up in ethyl acetate/water at pH 2.5. The organic layer was washed with water, dried over anhydrous sodium sulfate, and evaporated to dryness in vacuo to give 152 mg of the desired product.

EXAMPLE 14

[3S-[3α(Z),4β]]-3-[[(2-Amino-4-thiazolyl)[(1-carboxy-1-methylethoxy)imino]acetyl]amino]-4-methyl-N-(methylsulfonyl)-2-oxo-1-azetidinecarboxamide, dipotassium salt

[3S-[3α(Z),4β]]]-3-[[(2-Amino-4-thiazolyl)-[[2-(diphenylmethoxy)-1,1-dimethyl-2-oxoethoxy]imino]acetyl]amino]-4-methyl-N-(methylsulfonyl)-2-oxo-1-azetidinecarboxamide (152 mg; see example 13) was dissolved in dry dichloromethane. Anisole (135 μl) and trifluoroacetic acid (1 ml) was added, and the solution was stirred in an ice bath under dry nitrogen for 1.5 hours. The mixture was then evaporated to dryness in vacuo with the residue being evaporated in vacuo (four times) from dry acetonitrile to remove residual trifluoroacetic acid and anisole. The residue was taken up in ethyl acetate/water and 0.5 M pH 5.5 monobasic potassium phosphate buffer (2 ml). This was adjusted to pH 6.5 with dilute potassium hydroxide and extracted (two times) with ethyl acetate. The aqueous layer was evaporated to dryness in vacuo, and the residue was purified by chromatography on HP-20 resin (110 ml) using water. The product was lyophilized from water to give 82 mg, melting point 240° C.,dec.

Anal. for $C_{15}H_{18}N_6O_8S_2K_2.2 H_2O$ Calc'd: C, 30.60; H, 3.77; N, 14.28; S, 10.89. Found: C, 30.61; H, 3.43; N, 14.28; S, 10.51.

EXAMPLE 15

(S)-3-[[(1,1-Dimethylethoxy)carbonyl]amino]-N-(methylsulfonyl)-2-oxo-1azetidinecarbothioamide (A) (S)-3-[[(1,1-Dimethylethoxy)carbonyl]amino]-2-oxoazetidine (S)-3-Amino-2-azetidinone (21.77 g; see example 4A) and 30 g of triethylamine was dissolved in 200 ml of t-butanol and tetrahydrofuran (9:1). At 0° C. a solution of 37 g of bis(t-butyl)pyrocarbonate in 50 ml of tetrahydrofuran was dropped in; stirring for about 16 hours completed the reaction. The solvents were distilled off and the residue was dissolved in ethyl acetate. Extraction with aqueous citric acid and water yielded 25.3 g of the title compound from the organic phase.

(B) (S)-3-[[(1,1-Dimethylethoxy)carbonyl]amino]-N-(methylsulfonyl)-2-oxo-1-azetidinecarbothioamide Sec-Butyl lithium (9.25 ml of 1.35 M solution in cyclohexane) was added to a stirred solution of (S)-3-[[(1,1-dimethylethoxy)carbonyl]amino]-2-oxoazetidine (2.33 g) in 250 ml of dry tetrahydrofuran at −75° C. under nitrogen. After stirring for 2 minutes, (methylsulfonyl)-isothiocyanate (1.75 ml) was added, and the solution was stirred for 25 minutes at −75° C. and poured into 125 ml of 0.5 M pH 5.5 monobasic potassium phosphate buffer. Ethyl acetate and water were added, and the pH was adjusted to 2.5 (3N hydrochloric acid). The ethyl acetate layer was washed with water, dried with sodium sulfate, and evaporated to a residue (3.69 g), which was recrystallized from ethyl acetate to give 2.04 g of the title compound. Recrystallization of a portion from ethyl acetate gave crystals, melting point 181° C.,dec.

Anal. Calc'd for $C_{10}H_{17}N_3O_5S_2$: C, 37.15; H, 5.30; N, 13.00; S, 19.80. Found: C, 37.05; H, 5.34; N, 12.97; S, 19.76.

EXAMPLE 16

(S)-3-Amino-N-(methylsulfonyl)-2-oxo-1-azetidinecarbthioamide, trifluoroacetic acid salt (S)-3-[[(1,1-Dimethylethoxy)carbonyl]amino]-N-(methylsulfonyl)-2-oxo-1-azetidinecarbothioamide (323 mg) was stirred with 3 ml of trifluoroacetic acid at 0°–5° C. under nitrogen for 50 minutes. The solution was evaporated in vacuo to a residue, which was evaporated from acetonitrile (four times) to give the desired salt.

EXAMPLE 17

[3S(Z)]-3-[[(2-Amino-4-thiazolyl)(methoxyimino)acetyl]amino]-N-(methylsulfonyl)-2-oxo-1-azetidinecarbothioamide, potassium salt Triethylamine (162 μl) was added to a stirred suspension of (Z)-2-amino-α-(methoxyimino)-4-thiazole acetic acid (201 mg) in 3 ml of dry dimethylformamide at room temperature under nitrogen. After stirring for 2 minutes, the mixture was cooled to −25° C., and diphenyl chlorophosphate (208 μl, 1.0 mmol) was added. The mixture was stirred for 1.5 hours at −25° C. and added, using a syringe, to a stirred solution of (S)-3-amino-N-(methylsulfonyl )-2-oxo-1-azetidinecarbothioamide, trifluoroacetic acid salt (1.0 mmol; see example 16) and 0.70 ml of triethylamine in 3 ml of dimethylformamide at −25° C. under nitrogen. The reaction was stirred for 2.5 hours at this temperature and poured into 12 ml of 0.5 M pH 5.5 monobasic potassium phosphate buffer. Ethyl acetate and water were added, and the pH was adjusted to 7. The aqueous layer was adjusted to 2.5 (3N hydrochloric acid), and the solvents are removed in vacuo to give a residue, which was taken up in ethyl acetate and water (pH 2.5). Repeated extraction with ethyl acetate gave a combined ethyl acetate extract, which was dried (sodium sulfate), and evaporated to a residue. This residue was solubilized by addition of 5 ml of 0.5 M monobasic potassium phosphate buffer. Adjustment of the pH to 6.5, using dilute potassium hydroxide, and chromatograhy on a column of HP20AG resin (110 ml), using water as eluant, yielded 42 mg of the desired potassium salt as a residue. Treatment of a 36 mg portion of this sample with water and a small amount of acetone gave 31 mg of the desired potassium salt as crystals melting point 205° C.,dec.

Anal. Calc'd. for $C_{11}H_{13}N_6O_5S_3K.0.5\ H_2O$: C, 29.14; H, 3.11; N, 18.54; S, 21.17. Found: C, 29.40; H, 3.05; N, 18.52; S, 21.13.

EXAMPLE 18

[3S(Z)]-3-[[(2-Amino-4-thiazolyl)(methoxyimino)acetyl]amino]-N-(aminosulfonyl)-2-oxo-1-azetidinecarboxamide, ammonium salt

[3S(Z)]-3-[[[2-(Triphenylmethylamino)-4-thiazolyl][methoxyimino]acetyl]amino]-2-oxo-azetidine (0.51 g; see example 4B) was suspended in 10 ml of anhydrous acetonitrile. The mixture was cooled to −30° C. A solution fo. chlorosulfonyl isocyanate (0.18 g) in 5 ml of acetonitrile was added with stirring. The mixture was stirred at −30° C. for 30 minutes, the cooling bath was removed, and the mixture was stirred for an additional 60 minutes at 0° C. Ammonium carbonate (0.39 g) was added and the mixture was stirred at 0° C. for 1 hour and at room temperature for an additional 2 hours. The precipitate was filtered, yielding 1.26 g of crude [3S(Z)]-3-[[[2-(triphenylmethylamino)-4-thiazolyl][methoxyimino]acetyl]amino]-N-(aminosulfonyl)-2-oxo-1-azetidinecarboxamide, ammonium salt contaminated with some ammonium carbonate. The crude product was dissolved at room temperature in 12 ml of 70% formic acid and stirred for 90 minutes. The precipitate was filtered, the filtrate evaporated, the residue treated with water and adjusted to pH 6.5 with aqueous ammonia. The solution was filtered and freeze-dried. The freeze-dried product was purified by chromatography on HP-20 resin, eluting with water. The first 100 ml was discarded, 10 ml fractions were collected. Fractions 25–31 contain 60 mg of pure product. From fractions 32–40 additional 30 mg of slightly less pure product were obtained.

EXAMPLE 19

[3S(Z)]-3-[[(2-Amino-4-thiazolyl)(methoxyimino)acetyl]amino]-N-[[(1-methylethyl)amino]sulfonyl]-2-oxo-1-azetidinecarboxamide, sodium salt

[3S(Z)]-3-[[[2-(Triphenylmethylamino)-4-thiazolyl][methoxyimino]acetyl]amino]-2-azetidinone (1.02 g; see example 4B) was suspended in 10 ml of acetonitrile; the mixture was cooled to −30° C. A solution of chlorosulfonyl isocyanate (0.35 g) in 10 ml of acetonitrile was added with stirring. The mixture was stirred for 30 minutes at −30° C. and for an additional 60 minutes at 0° C. The solution was cooled to −10° C. and a solution of isopropylamine (0.5 g) in 5 ml of acetonitrile was added to form a clear solution. The cooling bath was removed and the mixture was stirred at 0° C. for 60 minutes. After evaporation to dryness, 2.2 g of crude [3S(Z)-3-[[[2-(triphenylmethylamino]-4-thiazolyl][methoxyimino]acetyl]amino]-N-[[(1-methylethyl)amino]-sulfonyl]-2-oxo-1-azetidinecarboxamide as the isopropylamine salt was obtained as a light syrup. The syrup was dissolved in 35 ml of 70% formic acid and stirred for 3 hours at room temperature. A precipitate (0.48 g) was removed by filtration and the filtrate was evaporated to dryness. The residue was treated with water, adjusted to pH 6.5 with 2N sodium hydroxide, and freeze-dried. The crude product was subjected to HP20AG chromatography (100–200 mesh) eluting with water (500 ml), then with water/acetone (8:2); 10 ml fractions are taken. The elution was monitored by thin-layer chromatography. Fractions 72–76 contained most of the product and were divided into three parts: fractions 72–74 contained 0.19 g of product, fraction 75 contained 0.36 g of product and fraction 76 contained 0.16 g of product. The product from fractions 72–74 and 76 was slightly less pure than the product from fraction 75.

EXAMPLE 20

(S)-N-(Aminosulfonyl)-2-oxo-3-[[(phenylmethoxy)carbonyl]amino]-1-azetidinecarboxamide Method I (S)-(2-Oxo-3-azetidinyl)carbamic acid, phenylmethyl ester (11 g; see example 1C) was dissolved in a mixture of 200 ml of acetonitrile and 50 ml of dichloromethane. The mixture was cooled to −50° C. and a solution of chlorosulfonyl isocyanate (9 g) in 25 ml of dichloromethane was added with stirring. After warming the mixture to −30° C. a solution of 6 g of ammonia in 160 ml of acetonitrile was added slowly. The reaction temperature was raised to −10° C. and finally to 0°–5° C.

The reaction time was 3 hours. The ammonium salt of the title compound precipitated and was filtered by suction (20 g). The crude product was purified by HP-20 chromatography (100–200 mesh) eluting with 2000 ml of water and water/acetone (8:2); 20 ml fractions are taken. The elution was monitored by thin-layer chromatography. From fractions 142–154, 9.3 g of product was obtained by evaporation.

The ammonium salt of the title compound was dissolved in 100 ml of water, layered with 200 ml of ethyl acetate and acidified. After separation and washing of the aqueous layer twice with ethyl acetate, the organic layer was washed with saturated sodium chloride solution, dried with anhydrous magnesium sulfate and evaporated to yield 8.1 g of the title compound.

Method II

A mixture of (S)-(2-oxo-3-azetidinyl) carbamic acid, phenylmethyl ester (11 g; see example 1C) in 175 ml of dichloromethane was cooled to −30° C. While stirring, 7.7 g of chlorosulfonyl isocyanate in 75 ml dichloromethane was added dropwise within 15 minutes. The temperature of the solution was allowed to rise to 0° C. over 30 minutes. Subsequently the clear solution was again cooled to −30° C. and 8.8 g of bis-(trimethylsilyl)amine dissolved in 30 ml of dichloromethane, was dropped in, while passing dry nitrogen through the flask. After an hour the reaction temperature was allowed to rise to −15° C. and was maintained for an additional 30 minutes. The solvent was distilled off in vacuo, and the residue was triturated with 400 ml of ether to give a solid (16.6 g) which was washed with an additional 20 ml ether. From the ethereal mother liquor there was obtained a second crop of 4.2 g of product.

The crude material (18.0 g) along with about 20 g of HP-20 resin was suspended in 30 ml of water and the mixture was chromatographed on an HP-20 column eluted with (a) 3 L of water; (b) 2.5 L of water/acetone (8:2); (c) 4 L of water/acetone (7:3); (d) 6 L of water/acetone (6:4). Fraction d yielded 6.2 g of the title compound melting point 150°–152° C.

EXAMPLE 21

(S)-N-(Aminosulfonyl)-3-[[(1,1-dimethylethoxy)carbonyl]amino]-2-oxo-1-azetidinecarboxamide, ammonium salt (S)-3-[[(1,1-Dimethylethoxy)carbonyl]amino]-2-oxoazetidine (5.1 g; see example 15A) was dissolved in a mixture of 160 ml of acetonitrile and 40 ml of dichloromethane. At −50° C. a solution of 5.4 g of chlorosulfonyl isocyanate in 30 ml of dichloromethane was added dropwise (15 minutes). The mixture was kept at −30° C. for 30 minutes. Then 64 ml of a solution of ammonia in acetonitrile (containing 2.4 g of ammonia)was added slowly at −10° to 0° C. The title compound precipitated together with inorganic material and was filtered by suction (crude yield 9.8 g). From the filtrate another crop of 2.7 g of crude title compound was obtained. According to thin-layer chromatography both fractions were of similar purity. The combined material was dissolved in 50 ml of water, adjusted to pH 6.5 by the addition of diluted aqueous ammonia and purified by chromatography on HP-20, eluting with water; 20 ml fractions were taken. Fractions 70–130 contained 2.7 g of the title compound.

EXAMPLE 22

(S)-3-Amino-N-(aminosulfonyl)-2-oxo-1-azetidine-carboxamide, inner salt

Method I:

(S)-N-(Aminosulfonyl)-3-[[(1,1-dimethylethoxy)carbonyl]amino]-2-oxo-1-azetidine-carboxamide, ammonium salt (2 g; see example 21) was added to 50 ml of trifluoroacetic acid at 0° C. The solution was stirred at 0° C. for 10 minutes and then for 30 minutes at room temperature, evaporated to dryness and the residue was treated with ether to yield 2.1 g of the trifluoroacetic acid salt of the title compound, contaminated with ammonium trifluoroacetate. 1.6 g of the trifluoroacetic acid salt of the title compound was suspended in 25 ml of acetonitrile. Addition of 6 ml of bis-trimethylsilylacetamide yields a clear solution from which, on the addition of 5 ml methanol, the title compound (0.58 g) precipitated.

Method II:

(S)-3-[[(1,1-Dimethylethoxy)carbonyl]-amino]-2-oxoazetidine (1.87 g; see example 15A) was dissolved in 50 ml of dichloromethane/acetonitrile (4:1) and cooled to −20° C.

Chlorosulfonyl isocyanate (1.42 g) in 15 ml of dichloromethane was added dropwise. Stirring was continued for 3 hours and a solution of 1.9 g of N-trimethylsilyl t-butylcarbamate in 20 ml of dichloromethane was added and the mixture was stirred for 10 hours at 0° C. After this time the solvents were distilled off and the residue was treated with ether/petroleum ether (3:1) yielding 2 g of crude (S)-3-[[(1,1-dimethylethoxy)carbonyl]amino]-N-[[(1,1-dimethylethoxy)carbonyl]amino]-2-oxo-1-azetidinecarboxamide as a crystalline material. This was stirred for 90 minutes in 20 ml trifluoroacetic acid/anisole (4:1) at −10° C. The reaction solution was then poured into 200 ml of ether; 2.3 g of solid was collected and dried. Suspension of this solid in dry acetonitrile and addition of 3 g of monosilyltrifluoroacetamide yielded a clear solution. To this solution 6 ml of methanol was added. The title compound precipitated from the solution immediately, yielded 0.76 g of product.

EXAMPLE 23

[3S(Z)]-N-(Aminosulfonyl)-3-[[(2-amino-4-thiazolyl)(methoxyimino)acetyl]amino]-2-oxo-1-azetidinecarboxamide, sodium salt (S)-3-Amino-N-(aminosulfonyl)-2-oxo-1-azetidinecarboxamide (see example 22, or prepared by hydrogenating 4.8 g of (S)-N-(aminosulfonyl)-3-[[(phenylmethoxy)carbonyl]amino]-2-oxo-1-azetidinecarboxamide used 2.5 g of 10% palladium on charcoal catalyst) was acylated using 4.22 g of (Z)-2-amino-α-(methoxyimino)-4-thiazoleacetic acid in 100 ml of dimethylformamide, 3.46 g of dicyclohexylcarbodiimide in 30 ml of dimethylformamide and 0.5 g of hydroxybenzotriazole. After 2.5 hours at room temperature the precipitated dicyclohexylurea was removed by filtration and the filtrate evaporated. The residue was triturated with 300 ml ethyl acetate to yield 4.2 g of insoluble material. After evaporation and trituration of the residue with ether another 1.6 g of solid was obtained. The combined solid material was suspended in water and the suspension adjusted to pH 6.5 with 1N sodium hydroxide, filtered and the filtrate subjected to HP-20 chromatography, eluting with water. The first 700 ml of eluate was discarded. Fractions 85-137 contain 1.04 g of the title compound. Another 0.3 g of slightly less pure material was obtained from fractions 70-84 and 138-150.

EXAMPLE 24

(S)-N-(Aminosulfonyl)-3-[[(phenylmethyl)carbonyl]amino]-2-oxo-1-azetidinecarboxamide (S)-3-Amino-N-(aminosulfonyl)-2-oxo-1-azetidinecarboxamide (see example 22, or prepared by hydrogenating 140 mg of (S)-N-(aminosulfonyl)-3-[[(phenylmethoxy)carbonyl]amino]-2-oxo-1-azetidinecarboxamide in dimethylformamide used 50 mg of 5% palladium on charcoal catalyst) was acylated with 100 mg of dicyclohexylcarbodiimide, 20 mg of hydroxybenzotriazole and 55 mg of benzeneacetic acid. The mixture was stirred at 0° C. for 6 hours and dicyclohexylurea was filtered off. Dimethylformamide was distilled off, the residue was dissolved in 5 ml of acetone and the solution was, after standing for about 16 hours, filtered and then evaporated. The crude material was chromatographed on an HP-20 column eluting with water/acetone (6:4) to give 45 mg of the title compound, melting point 137° C.

EXAMPLE 25

(S)-3-[[Phenylmethoxy)carbonyl]amino]-N-[[(phenylmethoxy)amino]sulfonyl]-2-oxo-1-azetidinecarboxamide, potassium salt (S)-(2-Oxo-3-azetidinyl)carbamic acid, phenylmethyl ester (5.1 g; see example 1C) was suspended in 80 ml of dry dichloromethane at −50° C. At this temperature 3.9 g chlorosulfonyl isocyanate dissolved in 25 ml of dichloromethane was dropped in with stirring. When the addition was complete, a clear solution was obtained and stirring was continued for 2 hours. Triethylamine (5.6 g) was added and 3.7 g of benzyloxyamine, dissolved in 20 ml of dichloromethane was added dropwise to the solution. The reaction mixture was stirred for about 16 hours at 0° C. Tetrabutylammoniumhydrogensulfate 8.5 g) dissolved in 150 ml of ice water was added and the pH was adjusted to 6.7 with 1N potassium hydroxide. The organic layer was separated, dried with sodium sulfate, and the solvent removed in vacuo. The oily residue was treated with 8.5 g of potassium perfluorobutanesulfonate in 50 ml of acetone. This solution was slowly poured into 200 ml of ether; crude product precipitated and was filtered off. Purification was achieved by reverse-phase chromatography using HP-20 and water/acetone 6:4 as eluent, yielding 3.2 g of product, melting point 200° C., dec.

EXAMPLE 26

[3S(Z)]-3-[[(2-Amino-4-thiazolyl)(methoxyimino)carbonyl]amino]-N-[[(phenylmethoxy)amino]-sulfonyl]-2-oxo-1-azetidinecarboxamide, potassium salt (S)-3-[[Phenylmethoxy)carbonyl]amino]-N-[[(phenylmethoxy)amino]sulfonyl]-2-oxo-1-azetidinecarboxamide, potassium salt (1.2; see example 25) was dissolved in 80 ml of dry dimethylformamide and hydrogenated in the presence of 0.75 g of palladium on charcoal. After 40 minutes the hydrogenation was complete. The catalyst was filtered off, and 0.55 g of (Z)-2-amino-α-(methoxyimino)-4-thiazoleacetic acid, 0.17 g of hydroxybenzotriazole and 1.03 g of dicyclohexylcarbodiimide was added. The solution was stirred at ambient temperature for about 16 hours. The precipitated urea was filtered off, the solvent removed in vacuo and the residue was chromatographed using HP-20 and water/acetone (9:1) as eluant. The product was a mixture of 50 mg of the title compound and 200 mg of [3S(Z)]-3-[[(2-amino-4-thiazolyl)-(methodyimino)carbonyl]amino]-N-(aminosulfonyl)-2-oxo-1-azetidinecarboxamide, potassium salt.

EXAMPLE 27

[3S(Z)]-N-(Aminosulfonyl)-3-[[(2-amino-4-thiazolyl)(ethoxyimino)acetyl]amino]-2-oxo-1-azetidionecarboxamide potassium salt (S)-N-(Aminosulfonyl)-2-oxo-3-[[(phenylmethoxy)carbonyl]amino]-1-azetidinecarboxamide, potassium salt (0.5 g; see example 20) was hydrogenated for 20 minutes in 70 ml of dry dimethyldormamide with 0.2 g of palladium on charcoal. (Z)-2-Amino-α-(ethoxyimino)-4-thiazoleacetic acid (0.36 g), 0.1 g of hydroxybenzotriazole and 0.62 g of dicyclohexylcarbodiimide were added and the solution was stirred for about 16 hours. The precipitated urea was filtered off, the solvent was removed and the residue was suspended in 5 ml of water. The pH was adjusted to 6.5 with 1N potassium hydroxide. This solution was immediately chromatographed using HP-20 and water as eluent, yielding 200 mg of the title compound, melting point 198°-200° C., dec.

EXAMPLE 28

[3S(R*)[-N-(Aminosulfonyl)-3-[[[[3-[(2-furanylmethylene)amino]-2-oxo-1-imidazolidinyl]carbonyl]amino]phenylacetyl]amino]-2-oxo-1-azetidinecarboxamide, potassium salt (S)-N-(Aminosulfonyl)-2-oxo-3-[[(phenylmethoxy)carbonyl]amino]-1-azetidinecarboxamide (0.8 g; see example 20) was dissolved in 80 ml of dry dimethylformamide and hydrogenated with 0.4 g of palladium on charcoal. After 20 minutes the catalyst was filtered off and 0.92 g of (R)-α-[[[3-[(2-furanylmethylene)amino]-2-oxo-1-imidazolidinyl]carbonyl]amino]-benzeneacetic acid, 0.16 g of hydroxybenzotriazole and 0.97 g of dicyclohexylcarbodiimide were added and the solution was stirred at ambient temperature for about 16 hours. The precipitated urea was filtered off and the solvent was removed in vacuo. The residue was chromatographed on HP-20 using water/acetone (7:3) as eluent. Freeze-drying of the appropriate fractions yields 200 mg of product. The potassium salt is prepared by dissolving the compound in water/acetone and adjusting the pH to 6.7 with 1N potassium hydroxide. The solution is freeze-dried.

EXAMPLE 29

[3S(R*)](Aminosulfonyl)-3-[[[[(4-ethyl-2,3-dioxo-1-piperazinyl)carbonyl]amino]phenylacetyl]-amino]-2-oxo-1-azetidinecarboxamide (S)-N-(Aminosulfonyl)-2-oxo-3-[[)phenylmethoxy)carbonyl]amino]-1-azetidinecarboxamide (0.8 g; see example 20) was hydrogenated in the presence of 0.4 g of palladium on charcoal. After 20 minutes the catalyst was filtered off and 0.82 g of (R)-α-[[(4-ethyl-2,3-dioxo-1-piperazinyl)carbonyl]amino]benzeneacetic acid, 0.16 g of hydroxybenzotriazole and 0.97 g of dicyclohexylcarbodiimide were added. The solution was stirred about 16 hours at ambient temperature. The precipitated urea was filtered off and the solvent was removed in vacuo. The residue was suspended in 10 ml of water-/acetone and the pH was adjusted to 6.5 with 1N potassium hydroxide.

EXAMPLE 30

[3S(Z)-2-[[[1-(2-Amino-4-thiazolyl-2-[[1-[[(methysulfonyl)amino]carbonyl]-2-oxo-3-azetidinyl]amino]-2-oxoethylidene]amino]oxy]-2-methylpropanoic acid, dipotassium salt (A) (S)-3-[[(1,1-Dimethylethoxy)carbonyl]amino]-N-(methylsulfonyl)-2-oxo-1-azetidinecarboxamide (S)-3-[[(1,1-Dimethylethoxy)carbonyl]amino]-2-azetidinone (1.12 g) was dissolved in dry tetrahydrofuran (120 ml) and stirred at −75° C. under dry nitrogen. sec-Butyl lithium (4.44 ml of a 1.35 M solution in cyclohexane) was added and followed in two minutes by methylsulfonyl isocyanate (0.72 ml). After stirring for 25 minutes at −75° C., the reaction was quenched by the addition of 0.5 M pH 5.5 monobasic potassium phosphate buffer (60 ml), diluted with ethyl acetate-water, acidified to pH 2.5 with 3N hydrochloric acid, and (60 ml), diluted with ethyl acetate-water, acidified to pH 2.5 with 3N hydrochloric acid, and extracted with ethyl acetate (three times). The extract was washed with water, dried over anhydrous sodium sulfate, and evaporated to dryness in vacuo to yield the desired product as a foam (1.73 g).

(B) (S)-3-Amino-N-(methylsulfonyl)-2-oxo-1-azetidinecarboxamide, trifluoroacetic acid salt (S)-3-[[(1,1-Dimethylethoxy)carbonyl]amino]-N-(methylsulfonyl)-2-oxo-1-azetidinecarboxamide (612 mg) was stirred with trifluoroacetic acid (6 ml) under nitrogen in an ice bath for 30 minutes. The solvent was removed in vacuo, and the residue was evaporated from acetonitrile (four times) to give the desired salt as a foam (638 mg).

(C) [3S(Z)]-2-[[[1-(2-Amino-4-thiazolyl)- 2-[[1-[[(methylsulfonyl) amino]carbonyl]-2-oxo- 3-azetidinyl-]amino]-2-oxoethylidene]amino]oxy]-2-methyl-propanoic acid, diphenylmethyl ester (Z) -(2-Amino-4-thiazolyl)[[2-(diphenylmethoxy)-1,1-dimethyl-2-oxoethoxy]imino]acetic acid (880 mg) in dry dimethylformamide (6ml) was stirred at −25° C. under nitrogen. Triethylamine (0.48 ml) was added, followed by diphenylchlorophosphate (0.62 ml), and the mixture was stirred at −25° C. for 55 minutes. This mixture was added to a stirred solution of the above mentioned crude trifluoroacetic acid salt (612 mg), and triethylamine (1.40 ml) in dry dimethylformamide (6 ml) at −25° C. under nitrogen. The reaction was stirred at 25° C. for 2.5 hours and quenched with 0.5 M pH 5.5 monobasic potassium phosphate buffer (24 ml). It was then diluted with ethyl acetate/water, acidified to pH 2.5, and extracted with ethyl acetate (three times). The ethyl acetate extract was washed with water, dried over anhydrous sodium sulfate, and evaporated to dryness in vacuo to yield a yellow solid (1.408 g). After chromatography on silica gel, using ethyl acetate-methanol, the product was taken up in ethyl acetate-water at pH 2.5 and extracted with ethyl acetate (three times). The extract was washed with water, dried over anhydrous sodium sulfate, and evaporated to dryness in vacuo to give the desired product as a solid (360 mg).

(D) [3S(Z)]-2-[[[1-(2-Amino-4-thiazolyl)- 2-[[1-[[(methylsulfonyl)amino]carbonyl]-2-oxo- 3-azetidinyl]amino]-2-oxoethylidene]amino]oxy]- 2- methyl-propanoic acid, dipostassium salt

[3S(Z)]-2-[[[1-(2-Amino-4-thiazolyl)- 2-[[1-[[(methylsulfonyl)amino]carbonyl]-2-oxo- 3-azetidinyl]amino]-2-oxoethylidene]amino]oxy]- 2-methylpropanoic acid, diphenylmethyl ester (360 mg) was dissolved in dry dichloromethane (10 ml) and stirred under dry nitrogen in an ice bath. Anisole (312 µl) and anhydrous trifluoroacetic acid (2 ml) were added, and the solution was stirred for 2 hours. The solvent was then removed in vacuo, and the residual solid was evaporated (four times) in vacuo from a solution in dry acetonitrile to remove traces of trifluoroacetic acid. The product was taken up in ethyl acetate-water. 0.5 M pH 5.5 monobasic potassium phosphate buffer (2 ml) was added, and the pH was adjusted to 6.5 with dilute potassium hydroxide. The organic layer was removed, and the aqueous layer was evaporated to a residue, which was combined with a similar residue, derived by treating a second portion (176 mg) of diphenylmethyl ester with trifluoroacetic acid-anisole. This crude potassium salt mixture was purified by chromatography on HP20AG, using water, to give the desired dipotassium salt as a powder (221 mg) after lyophilization, melting point 250°-° C., dec.

Anaylsis for $C_{14}H_{16}O_8N_6S_2 \cdot K_2 \cdot 3H_2O$
Calc'd: C,28.37; H, 3.74; N, 14.18; S, 10.82.
Found: C, 28.38; H, 3.58; N, 14.05; S, 10.82.

EXAMPLE 31

(S)-N-(1-Imidazolylsulfonyl)-2-oxo-3-[[(phenylmethoxy) carbonyl]amino]- 1-azetidinecarboxamide, potassium salt (S)-(2-Oxo-3-azetidinyl)carbamic acid, phenylmethyl ester (3 g) was suspended in 100 ml of dry dichloromethane and cooled to −5° C. Chlorosulfonyl isocyanate (2.1 g) in 10 ml of dichloromethane was dropped in with stirring, which was continued for 45 minutes. Triethylamine (3.5 g) and 1.02 g of imidazole were added and the solution was stirred overnight at 0° C. After the addition of 4.6 g of tetrabutylammonium hydrogen sulfate in 200 ml of ice water, the pH is adjusted to 6.5 with 1N potassium hydroxide. The organic layer was separated, dried (sodium sulfate), filtered and evaporated to dryness. The residue was treated with 4.6 g of potassium perfluorobutanesulfonate in 50 ml of acetone. This solution was poured into 200 ml of ether and crude product (4.5 g) was filtered off. Purification was accomplished by chromatography using HP20AG resin and water/acetone (8:2) as eluant, yielding 1.7 g of the title compound melting point 130° C., dec.

EXAMPLE 32

[3S(Z)]-3-[[(2-Amino-4-thiazolyl)(methoxyimino)-carbonyl]amino]-N-(1-imidazolylsulfonyl)-2-oxo-1-azetidinecarboxamide, potassium salt (S)-N-(1-Imidazolylsulfonyl)-2-oxo-3- [[(phenylmethoxy)carbonyl]amino]-1-azetidinecarboxamide, potassium salt (0.5 g; see example 31) was dissolved in 50 ml of dry dimethylformamide. After the addition of 0.2 g of 10% palladium on charcoal, hydrogen was bubbled through the mixture for 20 minutes. The catalyst was filtered off and 0.23 g of (Z)-2- amino-α-(methoxyimino)-4-thiazoleacetic acid, 0.05 g of hydroxybenzotriazole and 0.5 g of dicyclohexylcarbodiimide were added. The solution was stirred for 12 hours at room temperature. The precipitated urea was filtered off and the solvent was removed in vacuo. The residue was purified by HP20 chromatography using water/acetone

EXAMPLE 33

[3S(Z)]-2-[[[1-(2-Amino-4-thiazolyl)-2-
[[1-[[(aminosulfonyl)amino]carbonyl]-2-oxo-3-
azetidinyl]amino]-2-oxoethylidene]amino]oxy]-
2-methylpropanoic acid, disodium salt (S)-3-Amino-N-(aminosulfonyl)-2-oxo-1-azetidinecarboxamide, inner salt (see example 22) was reacted with 3.2 g (a 20% excess) of (Z) -(2-amino-4-thiazolyl)[[2-(diphenylmethoxy)- 1,1-dimethyl-2-oxoethoxy]imino]acetic acid in the presence of 1.5 g of dicyclohexylcarbodiimide and 0.2 g of N-hydroxybenzotriazole. The mixture was stirred for 5 hours at room temperature, the solution was evaporated and the residue was dissolved in ethyl acetate. The insoluble dicyclohexylurea was filtered off and the filtrate was washed three times with water and once with saturated sodium chloride solution, dried (magnesium sulfate) and evaporated to yield 4 g of crude [3S(Z)]-2-[[[1-(2-amino-4-thiazolyl)-2-[[1- [[(aminosulfonyl)amino]carbonyl]-2-oxo-3- azetidinyl]amino]-2-oxoethylidene]amino]oxy]-2-methylpropanoic acid, diphenylmethyl ester.

A portion of the crude was dissolved in 15 ml of anisole, cooled with stirring to −10° C. and 40 ml of trifluoroacetic acid was added. The mixture was stirred at −10° C. for an additional 30 minutes. Then, at −10° C., 100 ml of ether and 100 ml of petroleum ether were added to yield a precipitate (2.4 g). The precipitate was suspended in 50 ml of water at 0° C. and adjusted to pH 6.5 by the slow addition of 2N sodium hydroxide. Some insoluble material was removed by filtration and the filtrate freeze-dried to yield 2 g of crude product. The crude material was purified by HP20 AG chromatography eluting with water; 10 ml fractions were taken. From fractions 22-26, 0.63 g of pure product was obtained after freeze-drying. From fractions 20-21 and 27-29 another 0.39 g of less pure product was obtained.

EXAMPLE 34

[3S(Z)]-3-[[(2-Amino-4-thiazolyl) (methoxyimino)-acetyl]amino]-2-oxo-N-[(phenylamino)sulfonyl]-1-azetidinecarboxamide, sodium salt

[3S(Z)]-3-[[[2-(Triphenylmethylamino)-4- thiazolyl]methoxyimino]acetyl]amino]-2-oxo azetidine (1.02 g; see example 4B) was suspended in a mixture of 13 ml of acetonitrile and 13 ml of dichloromethane. At −50° C. a solution of chlorosulfonyl isocyanate (0.36 g) in 5 ml of dichloromethane was dropped in with stirring. The temperature was raised to −20° C. within 30 minutes. Addition of triethylamine (0.84 ml) immediately yielded a clear solution to which a solution of aniline (0.22 ml) was added. The reaction mixture was stirred at 0° C. for 60 minutes and at room temperature for another 60 minutes, then evaporated. The residue was suspended in water and the suspension was adjusted to pH 3.5 by the addition of 2N acetic acid. the insoluble crude [3S(Z)]-3-[[[(triphenylmethyl) amino]-4-thiazolyl] [methoxyimino]acetyl]-amino]-2-oxo-N-[(phenylamino)sulfonyl]-1-azetidinecarboxamide was isolated by filtration, yield 1.2.

To remove the trityl group, 1.1 g of [3S(Z)]-3-[[[2-(triphenylmethylamino)-4-thiazolyl]- [methoxyimino]acetyl]amino]-2-oxo-N-[(phenylamino)- sulfonyl]-1-azetidinecarboxamide was dissolved in 15 ml of tetrahydrofuran and 25 ml of 70% formic acid was added with cooling. After standing for 2 hours at room temperature the mixture was evaporated and the residue is treated with ether to yield 0.59 g of solid material. The solid was dissolved in 10 ml of tetrahydrofuran. Then 10 ml of water was added and the the mixture was adjusted to pH 6.5 by the addition of 2N sodium hydroxide. The tetrahydrofuran was removed by evaporation, the turbid water-phase was extracted once with ethyl acetate and freeze-dried. The crude material thus obtained was purified by HP20AG chromatography; 10 ml fractions were collected. It first eluted with water (fractions 1-80), then with water/acetone (95:5). From fractions 98-108, 70 mg of pure product was obtained.

EXAMPLE 35

[3S(Z)]-3-[[(2-Amino-thiazolyl) (methoxyimino)-acetyl]amino]-N-[(dimethylamino)sulfonyl]-2-oxo-1-azetidinecarboxamide, sodium salt Following the procedure of example 34, but substituting dimethylamine for aniline, yielded the title compound.

EXAMPLE 36

(S)-2-Oxo-3-[[(phenylmethoxy)carbonyl]amino]-N-[[(4-pyridyl)amino]sulfonyl]-1-azetidinecarboxamide, sodium salt (S)-(2-Oxo-3-azetidinyl)carbamic acid, phenylmethyl ester (6.6 g; see example 1C) was suspended in a mixture of 160 ml of acetonitrile and 40 ml of dichloromethane. To the suspension a solution of chlorosulfonyl isocyanate (5.1 g) in 15 ml dichloromethane was added at −50° C. with stirring. The mixture was stirred for 1 hour at −30° to −25° C. A clear solution of (S)-N-[(chlorosulfonyl)amino]-2-oxo-3 -[[(phenylmethoxy)-carbonyl]amino]-1-azetidinecarboxamide formed to which 12.4 ml of triethylamine was added, followed by a suspension of (4-pyridyl)amine (3.4 g) in 40 ml of a 1:1 mixture of acetonitrile and dichloromethane. The temperature was raised to 0°-5° C. and the mixture was stirred at this temperature for 90 minutes. A clear solution formed, from which crystals precipitated. After stirring for an additional 2 hours at room temperature the precipitate was filtered by suction, suspended in water and the pH of the suspension was adjusted to pH 3.5. After stirring for 30 minutes, the precipitate was filtered, washed with water and dried to yield 8 g of the title compound. From the organic filtrate a second crop of 3.4 g of less pure product was obtained by evaporation, suspension in water, adjustment of the suspension to pH 3.5 and filtration.

EXAMPLE 37

(S)-N-[(Methylamino)sulfonyl]-2-oxo-3-[[(phenylmethoxy)carbonyl]amino]-1-azetidinecarboxamide (S)-(2-Oxo-3-azetidinyl)carbamic acid, phenylmethyl ester (6.6 g; see example 1C) was suspended in a mixture of 160 ml of acetonitrile and 40 ml of dichloromethane. Then, at −50° C., chlorosulfonyl isocyanate (5.1 g) dissolved in 15 ml of dichloromethane, was added with stirring. After stirring for 1 hour at −30° C., a solution of 6 g of methylamine in 50 ml of acetonitrile was added so that an excess of amine was avoided (pH ca. 6.5) (40 ml of the solution was required). After stirring for 90 minutes at −10° C. and 90 minutes at 0° C. the precipitate was filtered to yield 10.5 g of a solid. Evaporation of the filtrate yielded another 5.2 g of a foam. Accord- (9:1), yielding 0.3 g of the title compound, melting point 210° C., dec.

ing to the spectra (NMR, IR) both contained the methylammonium salt of the title compound. The combined material was purified by chromatography on HP20AG. The methylammonium salt of the title compound was eluted with water/acetone (80:20) to yield 4.6 g of pure material. From the methylammonium salt, the title compound was prepared by dissolving it in water (50 ml), layering with ethyl acetate and acidifying the mixture with cooling and stirring. From the organic layer, 3.5 g of the title compound was obtained.

EXAMPLE 38

(S)-3-Amino-N-[(methylamino)sulfonyl]-2-oxo-1-azetidinecarboxamide, inner salt (S)-N-[(Methylamino)sulfonyl]-2-oxo-3-[[(phenylmethoxy)carbonyl]amino]-1-azetidinecarboxamide (2.1 g; see Example 37) was suspended in 25 ml of acetonitrile and bis(trimethylsilyl)acetamide (3.3 g) was added. The solution was added to a suspension of 1 g of 10% palladium on charcoal in 25 ml of acetonitrile, through which hydrogen was passed for 30 minutes prior to the addition of the solution of the starting azetidinone. After 15 minutes the catalyst was removed by filtration and 2 ml of methanol was added to the filtrate to precipitate 1.3 g of the title compound.

EXAMPLE 39

(S)-3-Amino-2-oxo-N-[[(4-pyridyl)amino]sulfonyl]-1-azetidinecarboxamide (S)-2-Oxo-3-[[(phenylmethoxy)carbonyl]amino]-N-[[(4-pyridyl)amino]sulfonyl]-1-azetidinecarboxamide (2.1 g; see example 36) was suspended in 25 ml of acetonitrile and 3 g (3.6 ml) of bis(trimethylsilyl)acetamide was added with stirring. After a few minutes a clear solution was formed. This solution was added to a suspension of 1 g of 10% palladium on charcoal in 25 ml of acetonitrile, through which hydrogen was passed for 30 minutes prior to the addition of the solution of the starting azetidinone. Hydrogenation was complete after 70 minutes. The catalyst was removed by filtration. On addition of 1 ml of methanol the title compound crystallized from the solution; yield 1.0 g.

EXAMPLE 40

[3S(Z)]-3-[[(2-Amino-4-thiazolyl)(methoxyimino)acetyl]amino]-2-oxo-N-[[(4-pyridyl)amino]sulfonyl]-1-azetidinecarboxamide (S)-3-Amino-2-oxo-N-[[(4-pyridyl)amino]sulfonyl]-1-azetidinecarboxamide (0.57 g; see Example 39) was dissolved in 10 ml of dimethylformamide and added to a mixture of (Z)-2-amino-α-(methoxyimino)-4-thiazoleacetic acid (0.6 g), dicyclohexylcarbodiimide (0.49 g) and N-hydroxybenzotriazole (60 mg) in 20 ml of dimethylformamide and stirred at room temperature. After 2 hours the conversion was complete. Dicyclohexylurea was removed by filtration and the filtrate was evaporated and treated with ether to yield 1.3 g of a solid. The solid was dissolved in a mixture of 15 ml of water and 15 ml of acetone and adjusted to pH 6.5 by the addition of a solution of sodium bicarbonate. On removal of the acetone by evaporation, 0.5 g of the title compound precipitated from the aqueous phase, melting point, 221° C., dec.

EXAMPLE 41

[3S(Z)]-2-Amino-N-[1-[[[(dimethylamino)sulfonyl]amino]thioxomethyl]-2-oxo-3-azetidinyl]-α-(methoxyimino)-4-thiazoleacetamide (A) (S)-3-[[(1,1-Dimethylethoxy)carbonyl]amino]-N-[[[1-(dimethylamino)sulfonyl]amino]thioxomethyl]-2-oxoazetidine (S)-3-[[(1,1-Dimethylethoxy)carbonyl]amino-2-oxoazetidine (0.93 g, 0.005 mole) and triethylamine (1.35 ml, 0.01 mole) were dissolved in 20 ml of dry acetonitrile at 0° C. [Dimethylamino(sulfonyl)]isothiocyanate (1.09 ml, 0.01 mole) was added dropwise and the reaction was stirred at 0° C. for 3 hours and at room temperature overnight. The reaction mixture was concentrated in vacuo. To the residue was added 10 ml of 0.5N pH 5.5 KH$_2$PO$_4$ and 5 ml of water. The pH was adjusted to 2.8 with dilute acid (1N HCl), and product was extracted with 3 200 ml portions of ethyl acetate. The ethyl acetate was concentrated in vacuo and product was recrystallized from methanol to yield 0.76 g, melting point 184° C., dec.

(B) (S)-3-Amino-N-[[[(dimethylamino)sulfonyl]amino]-thioxomethyl]-2-oxoazetidine, trifluoroacetic acid salt The above thioxomethyl azetidine (0.352 g, 0.001 mole) was dissolved in 3 ml of trifluoroacetic acid and stirred at 0° for 2 hrs. The solution was concentrated in vacuo, and the residue was evaporated from acetonitrile (3X) to give the desired product.

(C) [3S(Z)]-2-Amino-N-[1-[[[(dimethylamino)sulfonyl]amino]thioxomethyl]-2-oxo-3-azetidinyl]-α-(methoxyimino)-4-thiazoleacetamide, potassium salt To a solution of (2-amino-4-thiazolyl)methoxyimino acetic acid (0.266 g, 0.001 mole) in 3 ml dry DMF (dimethylformamide) was added triethylamine (0.153 ml, 0.001 mole) under N$_2$. This solution was cooled to −25° C. and diphenyl chlorophosphate (0.207 ml, 0.001 mole) was added. The reaction mixture was stirred at −25° C. for 1 hr. The above crude trifuloroacetic acid salt and triethylamine (0.7 ml) were dissolved in 3 ml of DMF. The above mixed anhydride was added via syringe to this solution at −50° C. to −25° C. After 3 hrs. the solution was poured into 12 ml of 0.5M pH 5.5 KH$_2$PO$_4$ buffer, and the pH was adjusted to 7.8 with dilute KOH. The DMF and water were evaporated off in vacuo and the pot residue was dissolved in 20 ml of water and washed with ethyl acetate. The aqueous solution was acidified to pH 2.8 and product was extracted with two portions of ethyl acetate. This was dried (Na$_2$SO$_4$), filtered, and concentrated in vacuo. The product was purified by chromatographing twice through two 60 ml portions of HP-20 resin using water as eluant. The aqueous fractions containing product (Rydon positive) were lyophilized to give 109 mg of analytical product, after drying at 45° C./1 mm for 4 hours, having m.p. 204°-208° C., dec.

EXAMPLE 42

[3S(R)]-4-Ethyl-N-[2-[[1-[[(methylsulfonyl)amino]carbonyl]-2-oxo-3-azetidinyl]amino]-2-oxo-1-phenylethyl]-2,3-dioxo-1-piperazinecarboxamide By substituting (R)-α-[[(4-ethyl-2,3-dioxo-1-piperazinyl)carbonyl]amino]phenyl acetyl chloride for the phenylacetyl chloride used in Example 7, the titled product was obtained as an amorphous solid, m.p. 181-185° C. as the sodium salt.

EXAMPLE 43

[3S-[3α(R), 4β]]-4-Ethyl-N-[2-[[2-methyl-1-[[(methylsulfonyl)amino]carbonyl]2-oxo-3-azetidinyl]amino]-2-oxo-1phenylethyl-2,3-dioxo-1-piperazinecarboxamide By reacting (R)-α-[[4-ethyl-2,3-dioxo-1-piperazinyl)carbonyl]amino]phenyl acetic acid and [3S-[3α,4β]]-3-amino-4-methyl-N-(methylsulfonyl)-2-oxo-1-azetidinecarboxamide (from Example 11) according to the procedure of Example 7, the titled product was obtained as a solid, m.p. 170° C., dec., as the sodium salt.

EXAMPLE 44

[3S(R)]-3-[Aminophenylacetyl)amino]-N-methylsulfonyl)-2-oxo-1-azetidinecarboxamide By substituting α-amino-phenyl acetic acid for the (2-amino-4thiazolyl)-(methoxyimino)acetic acid used in Example 12, the titled product was obtained, m.p. 149° C., dec., as the trifluoroacetic acid salt.

EXAMPLE 45

[3S(Z)]-2-Amino-N-[1-[[[(4-aminophenyl)sulfonyl]amino]carbonyl]-2-oxo-3-azetidinyl]α-(methoxyimino)-4-thiazoleacetamide By substituting (S)-3-amino-N-[(4-aminophenyl)sulfonyl]-2-oxo-1-azetidinecarboxamide for the azetidinecarboxamide used in Example 12 the titled product was obtained as a solid (potassium salt) m.p. 220' C., dec.

EXAMPLE 46

[3S(Z)]-2-[[[1-(2-Amino-4-thiazolyl)-2-[[1-[[(1H-imidazol-1-ylsulfonyl)amino]carbonyl]-2-oxo-3-azetidinyl]amino]-2-oxoethylidene]-amino]oxy]-2-methylpropanoic acid By following the procedure of Example 33, substituting (S)-N-(1-imidazolylsulfonyl)-2-oxo-1-azetidinecarboxamide for the azetidinecarboxamide used therein, the titled product was obtained, m.p. potassium salt 240° C. dec., as the potassium salt.

EXAMPLE 47

[3S(R)]-4-Ethyl-N-[2-[[1-[[(1H-imidazol-1-ylsulfonyl)amino[carbonyl]-2-oxo-3-azetidinyl]amino]-2-oxo-1-phenylethyl]-2,3-dioxo-1-piperazinecarboxamide By reacting (S)-N-(1-imidazolylsulfonyl)-2-oxo-1-azetidinecarboxamide and (R)-α-[[4-ethyl-2,3-dioxo-1-piperazinyl)carbonyl]amino]phenylacetic acid in the presence of dicyclohexylcarbodiimide and N-hydroxybenzotriazole according to the procedure of Example 33, the titled product was obtained, m.p. 175° C., dec., as the potassium salt.

EXAMPLE 48

[3S(Z)-2-amino-N-[1-[[[thiazol-2-ylamino)sulfonyl]amino]thioxomethyl]-2-oxo-3-azetidinyl[-α-(methoxyimino)-4-thiazoleacetamide By substituting (S)-3-amino-2-oxo-N-[[(2-thiazolinyl)amino]sulfonyl]-1-azetidinecarboxamide for the carboxamide used in Example 40, the titled compound was obtained, m.p. 250° C., dec., as the sodium salt.

EXAMPLE 49

[3S(Z)-2-amino-N-[1-[[[5-methyl-1,3,4-thiadiazol-2-ylamino]sulfonyl]amino]thioxomethyl]-2-oxo-3-azetidinyl]-α-(methoxyimino)-4-thiazoleacetamide By substituting (S)-3-amino-2-N-[[(5-methyl-1,3,4-thiadiazol-2-yl)amino]sulfonyl]-1-azetidinecarboxamide for the carboxamide used in Example 40, the titled compound was obtained, m.p. 209-212° C.

EXAMPLE 50

By substituting the carboxylic acids containing the acyl groups shown in the first column of Table I into Example 23 for the acid used therein (2-amino-60 -(methoxyimino)-4-thiazoleacetic acid), and in the case of parts (j) through (o), substituting the azetidinecarboxamide containing the R-radical indicated, for the azetidinecarboxamide used in Example 23 the products shown in Table I are obtained.

TABLE 1 acyl-NH—[azetidinone]—N—CO—NH—SO$_2$—R

| | Acyl | —R | m.p. °C. |
|---|---|---|---|
| (a) | H$_2$N-thiazole-C(=N-OC$_2$H$_5$)-CO— | —NH$_2$ | 200 d. K$^+$ salt |
| (b) | H$_2$N-CO-CO-NH-CH(C$_6$H$_5$)-CO—* | —NH$_2$ | 212 d. K$^+$ salt |
| (c) | C$_2$H$_2$N-[2,3-dioxopiperazinyl]-CO-NH-CH(C$_6$H$_5$)-CO— | —NH$_2$ | 185 d. K$^+$ salt |

TABLE 1-continued acyl-NH—[β-lactam]—N—CO—NH—SO$_2$—R

| | Acyl | —R | m.p. °C. |
|---|---|---|---|
| (d) | 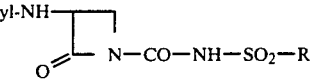 2,6-dichloropyridin-4-yl—S—CH$_2$CO— | —NH$_2$ | 100–105° |
| (e) | 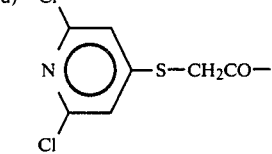 C$_6$H$_5$—CH(OH)—CO— | —NH$_2$ | 132–135° d. |
| (f) |  C$_6$H$_5$—CH(COOH)—CO— | —NH$_2$ | 145° d. |
| (g) |  C$_6$H$_5$—CH(NH—CO—N(—N=CH-furyl)—)—CO— (with ring C=O) | —NH$_2$ | 245° d. K$^+$ salt |
| (h) | 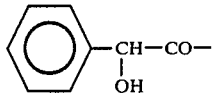 C$_6$H$_5$—CH(NH$_2$)—CO— | —NH$_2$ | 216° d. .CF$_3$COOH |
| (i) |  2-amino-thiazol-4-yl—C(=N—OC$_2$H$_5$)—CO— | —NH$_2$ | 204–207° d. |
| (j) |  2-amino-thiazol-4-yl—C(=N—OCH$_3$)—CO— | —NHCH$_2$CH$_2$OCOCH$_3$ | 200° d. K$^+$ salt |
| (k) | 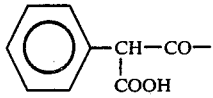 2-amino-thiazol-4-yl—C(=N—OCH$_3$)—CO— | —NH—(CH$_2$)$_3$—N(CH$_3$)$_2$ | 160° d. |
| (l) |  2-amino-thiazol-4-yl—C(=N—OCH$_3$)—CO— | —NH—CH$_2$—CO—NH$_2$ | 211–213° K$^+$ salt |

TABLE 1-continued acyl-NH—⟨azetidinone⟩—N—CO—NH—SO₂—R

| | Acyl | —R | m.p. °C. |
|---|---|---|---|
| (m) | C₆H₅CH₂O—CO— | —NH—NH—COO—tC₄H₉ | 130° d. |
| (n) | H₂N-thiazolyl-C(=N-OCH₃)—CO— | —NH—NHCOCH₃ | 182–200° d. K⁺ salt |
| (o) | H₂N-thiazolyl-C(=N-OCH₃)—CO— | —NH—NH₂ | 150° d. K⁺ salt |
| (p) | H₂N-thiazolyl-C(=N-OCH₃)—CO— | —NHCH₂CH₂—N⟨imidazolidine-2,4-dione⟩N— | 179–184 d. K⁺ salt |
| (q) | H₂N-thiazolyl-C(=N-OCH₃)—CO— | —NHCH₂CH₂NHCOCH₃ | 152 d. K⁺ salt |

*as used herein, the designation C₆H₅ represents phenyl.

EXAMPLE 51

By substituting the carboxylic acids containing the acyl groups shown in the first column of Table II into Example 23 for the acid used therein, and substituting the azetidinecarboxamide containing the R-radical indicated for the azetidinecarboxamide used in Example 23 the products shown in Table II were obtained. In the general formula Y can be hydrogen, alkyl, substituted alkyl, phenyl, substituted phenyl, phenylalkyl or (substituted phenyl) alkyl.

TABLE II acyl-NH—CH(R₃)—⟨azetidinone⟩—N—CO—NH—SO₂—N⟨ring with 2 C=O⟩N—Y

| | Acyl | R₃ | Y | m.p. °C. |
|---|---|---|---|---|
| (a) | H₂N-thiazolyl-C(=N—O—C₂H₅)—CO— | H | —C₂H₅ | 208° d. K⁺ salt |
| (b) | H₂N-thiazolyl-C(=N—OCH₃)—CO— | H | —C₂H₅ | 202° d. K⁺ salt |
| (c) | C₂H₅N⟨ring⟩N—CO—NH—CH(C₆H₅)—CO— | H | —C₂H₅ | 178° d. K⁺ salt |

TABLE II-continued

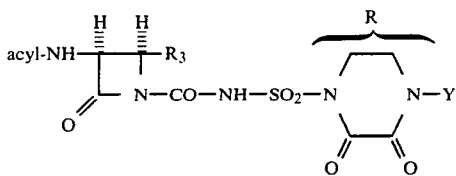

| | Acyl | $R_3$ | Y | m.p. °C. |
|---|---|---|---|---|
| (d) | H₂N—[thiazole]—C(=N—O—C(CH₃)₂—COOH)—CO— | H | —C₂H₅ | 220° d. K⁺ salt |
| (e) | H₂N—[thiazole]—C(=N—OCH₃)—CO— | H | —iC₃H₇ | 235–238° K⁺ salt |
| (f) | C₂H₅N[piperazine]N—CO—NH—CH(C₆H₅)—CO— | H | —iC₃H₇ | 193° d. K⁺ salt |
| (g) | H₂N—[thiazole]—C(=N—O—C(CH₃)₂—COOH)—CO— | H | —iC₃H₇ | 237° d. K⁺ salt |
| (h) | H₂N—[thiazole]—C(=N—O—iC₃H₇)—CO— | H | —C₂H₅ | 201° d. K⁺ salt |
| (i) | H₂N—[thiazole]—C(=N—O—CH₂CF₃)—CO— | H | —C₂H₅ | 180° d. K⁺ salt |
| (j) | H₂N—[thiazole]—C(=N—O—C(CH₃)₂—COOH)—CO— | —CH₃ | —C₂H₅ | 231° d. K⁺ salt |
| (k) | H₂N—[thiazole]—C(=N—OCH₃)—CO— | H | —C₆H₅ | 175–180° K⁺ salt |

TABLE II-continued

![Structure: acyl-NH-CH(H)-CH(H)(R3)-C(O)-N-CO-NH-SO2-N(ring with R bracket, two C=O, N-Y)]

| | Acyl | R3 | Y | m.p. °C. |
|---|---|---|---|---|
| (l) | H2N-C(S)=N- thiazole -C(=N-O-C(CH3)2-COOH)-CO- | H | —C6H5 | 222–228° K+ salt |
| (m) | H2N-C(S)=N- thiazole -C(=N-OH)-CO- | H | —C2H5 | 207° d. K+ salt |

EXAMPLE 52

By substituting the carboxylic acids containing the acyl groups shown in the first column of Table III into Example 23 for the acid used therein, and substituting the azetidinecarboxamide containing the R-radical indicated for the azetidinecarboxamide used in Example 23, the products shown in Table III were obtained. In the general formula, n can be zero or one and X can be methylene, oxygen or a nitrogen atom which can be substituted with alkyl, substituted alkyl, phenyl, substituted phenyl, phenylalkyl, (substituted phenyl)alkyl, amino, alkylamino, dialkylamino, alkylidenamino, aralkylidenamino, alkylsulfonyl, carboxy, carboxyalkyl and the like.

TABLE III

![Structure: acyl-NH-azetidinone-N-CO-NH-SO2-(NH)n-N-C(=O)-X ring]

| | Acyl | X | n | m.p. °C. |
|---|---|---|---|---|
| (a) | C6H5CH2OCO— | N—H | 0 | 158 d. K+ salt |
| (b) | H2N-C(S)=N- thiazole -C(=N-OCH3)-CO— | N—H | 0 | 252 d. K+ salt |
| (c) | C2H5N(piperazine)N-CO-NH-CH(C6H5)-CO— with two C=O | N—H | 0 | 187 d. K+ salt |
| (d) | H2N-C(S)=N- thiazole -C(=N-O-C(CH3)2-COOH)-CO— | N—H | 0 | 230 |

TABLE III-continued acyl-NH—[β-lactam]—N—CO—NH—SO$_2$—(NH)$_n$—N—[ring]—X (with C=O)

| Acyl | X | n | m.p. °C. |
|------|---|---|----------|
| (e) H$_2$N-(thiazole)-C(=N-OCH$_3$)-CO— | N—SO$_2$CH$_3$ | 0 | 210 d. K+ salt |
| (f) C$_2$H$_5$N-(dioxopiperazine)-N—CO—NH—CH(C$_6$H$_5$)—CO— | N—SO$_2$CH$_3$ | 0 | 187 d. K+ salt |
| (g) H$_2$N-(thiazole)-C(=N-O-C(CH$_3$)$_2$-COOH)-CO— | N—SO$_2$CH$_3$ | 0 | 227 K+ salt |
| (h) C$_2$H$_5$N-(dioxopiperazine)-N—CO—NH—CH(C$_6$H$_5$)—CO— | N—iC$_3$H$_7$ | 0 | 183 d. K+ salt |
| (i) H$_2$N-(thiazole)-C(=N-O-C(CH$_3$)$_2$-COOH)-CO— | N—iC$_3$H$_7$ | 0 | 252 d. K+ salt |
| (j) H$_2$N-(thiazole)-C(=N-OCH$_3$)-CO— | N—N=CH—C$_6$H$_5$ | 0 | 253 d. K+ salt |
| (k) C$_2$H$_5$N-(dioxopiperazine)-N—CO—NH—CH(C$_6$H$_5$)—CO— | N—N=CH—C$_6$H$_5$ | 0 | 176 d. K+ salt |
| (l) H$_2$N-(thiazole)-C(=N-OCH$_3$)-CO— | N—C$_2$H$_5$ | 0 | 183 d. K+ salt |

TABLE III-continued

| Acyl | X | n | m.p. °C. |
|---|---|---|---|
| (m) C₂H₅N-piperazine-2,3-dione-CO-NH-CH(C₆H₅)-CO- | N-C₂H₅ | 0 | 179 d. K+ salt |
| (n) aminothiazolyl-C(=N-O-C(CH₃)₂-COOH)-CO- | N-C₂H₅ | 0 | 232 d. K+ salt |
| (o) aminothiazolyl-C(=N-OCH₃)-CO- | N-C₆H₅ | 0 | 222 d. K+ salt |
| (p) aminothiazolyl-C(=N-OCH₃)-CO- | N-CH₂-C₆H₅ | 0 | 197 d. K+ salt |
| (q) C₂H₅N-piperazine-2,3-dione-CO-NH-CH(C₆H₅)-CO- | N-C₆H₅ | 0 | 186 d. K+ salt |
| (r) aminothiazolyl-C(=N-O-C(CH₃)₂-COOH)-CO- | N-C₆H₅ | 0 | 230 d. K+ salt |
| (s) C₂H₅N-piperazine-2,3-dione-CO-NH-CH(C₆H₅)-CO- | N-CH₂C₆H₅ | 0 | 175 d. K+ salt |
| (t) aminothiazolyl-C(=N-O-C(CH₃)₂-COOH)-CO- | N-CH₂-C₆H₅ | 0 | 207 d. K+ salt |

TABLE III-continued acyl-NH—[structure]—N—CO—NH—SO$_2$—(NH)$_n$—N—[structure]—X

| Acyl | X | n | m.p. °C. |
|---|---|---|---|
| (u) H$_2$N-thiazole-C(=N-OCH$_3$)-CO- | N—COOtC$_4$H$_9$ | 0 | 170–175 d. K+ salt |
| (v) H$_2$N-thiazole-C(=N-OCH$_3$)-CO- | N—CH$_2$CH$_2$NH$_2$ | 0 | 198–203 d. K+ salt |
| (w) C$_2$H$_5$N-piperazine-dione-CO—NH—CH(C$_6$H$_5$)—CO- | N—CH$_2$CH$_2$NH$_2$ | 0 | 188–193 d. K+ salt |
| (x) H$_2$N-thiazole-C(=N—O—C(CH$_3$)$_2$—COOH)-CO- | N—CH$_2$CH$_2$NH$_2$ | 0 | 202–205 d. K+ salt |
| (y) H$_2$N-thiazole-C(=N-OCH$_3$)-CO- | N—NH$_2$ | 0 | 190–195 d. K+ salt |
| (z) C$_2$H$_5$N-piperazine-dione-CO—NH—CH(C$_6$H$_5$)—CO- | N—N=iC$_3$H$_7$ | 0 | 183–188 d. K+ salt |
| (aa) H$_2$N-thiazole-C(=N-OCH$_3$)-CO- | CH$_2$ | 0 | 200 d. K+ salt |
| (bb) C$_2$H$_5$N-piperazine-dione-CO—NH—CH(C$_6$H$_5$)—CO- | CH$_2$ | 0 | 187 d. K+ salt |

TABLE III-continued $$\text{acyl-NH} - \boxed{\phantom{X}} - \text{N}-\text{CO}-\text{NH}-\text{SO}_2-(\text{NH})_n-\text{N}\overset{\displaystyle\text{O}}{\underset{\displaystyle\phantom{X}}{\diagdown}}\!\!\!\!\!\!-\text{X}$$

| Acyl | X | n | m.p. °C. |
|---|---|---|---|
| (cc) H$_2$N-thiazole-CH=C(CO-)(N-O-C(CH$_3$)$_2$-COOH) | CH$_2$ | 0 | 245 d. K+ salt |
| (dd) H$_2$N-thiazole-CH=C(CO-)(N-OH) | CH$_2$ | 0 | 202 K+ salt |
| (ee) H$_2$N-thiazole-CH=C(CO-)(N-OC$_2$H$_5$) | CH$_2$ | 0 | 195 d. K+ salt |
| (ff) H$_2$N-thiazole-CH=C(CO-)(N-OCH$_3$) | O | 0 | 184 d. K+ salt |
| (gg) C$_2$H$_5$N(piperazinedione)N-CO-NH-CH(C$_6$H$_5$)-CO- | O | 0 | 176 d. K+ salt |
| (hh) H$_2$N-thiazole-CH=C(CO-)(N-O-C(CH$_3$)$_2$-COOH) | O | 0 | 259 d. K+ salt |
| (ii) H$_2$N-thiazole-CH=C(CO-)(N-OCH$_3$) | O | 1 | 200 d. K+ salt |
| (jj) H$_2$N-thiazole-CH=C(CO-)(N-OCH$_3$) | NH | 1 | 220 d. K+ salt |

EXAMPLE 53

By substituting the carboxylic acids containing the acyl groups shown in the first column of Table IV into Example 23 for the acid used therein, and substituting the azetidinecarboxamide containing the R-radical indicated for the azetidine carboxamide used in Example 23, the products shown in Table IV were obtained. In the general formula, W can be hydrogen, alkyl, substituted alkyl, phenyl, substituted phenyl, phenylalkyl or (substituted phenyl)alkyl.

TABLE IV

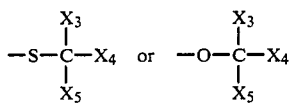

| | Acyl | W | m.p. °C. |
|---|---|---|---|
| (a) | C$_2$H$_5$N(CO)$_2$—N—CO—NH—CH(C$_6$H$_5$)—CO— | H | 221 d. K+ salt |
| (b) | H$_2$N-thiazole-C(=N—O—C(CH$_3$)$_2$COOH)—CO— | H | 198 d. K+ salt |
| (c) | H$_2$N-thiazole-C(=N—OCH$_3$)—CO— | H | 247 d. K+ salt |
| (d) | H$_2$N-thiazole-C(=N—OCH$_3$)—CO— | CH$_3$ | 212 d. K+ salt |
| (e) | C$_2$H$_5$N(CO)$_2$—N—CO—NH—CH(C$_6$H$_5$)—CO— | CH$_3$ | 197 d. K+ salt |
| (f) | H$_2$N-thiazole-C(=N—O—C(CH$_3$)$_2$COOH)—CO— | CH$_3$ | 235 d. K+ salt |

What is claimed is:

1. A β-lactam having the formula

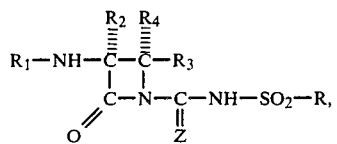

or a pharmaceutically acceptable salt thereof; wherein

R is alkyl, alkenyl, alkynyl, substituted alkyl, phenyl, substituted phenyl, a 5, 6 or 7-membered heterocycle, phenylalkyl, (substituted phenyl)alkyl, (5, 6 or 7-membered heterocycle)alkyl, or —NR$_a$R$_b$ wherein R$_a$ AND R$_b$ are the same or different and each is hydrogen, alkyl, substituted alkyl, phenyl, substituted phenyl, phenylalkyl, or (substituted phenyl)alkyl or one of R$_a$ and R$_b$ is hydrogen, alkyl, phenyl, substituted phenyl, phenylalkyl or (substituted phenyl)alkyl and the other is amino, alkanoylamino, arylcarbonylamino, alkoxycarbonylamino, alkysulfonylamino, alkylamino, dialkylamino, phenylamino, (substituted phenyl)amino, hydroxy, cyano, alkoxy, phenyloxy, (substituted phenyl)oxy, phenylalkoxy, (substituted phenyl)-alkoxy, a 5, 6 or 7-membered heterocycle, (5, 6 or 7-membered heterocycle)alkyl, (5, 6 or 7-membered heterocycle)alkoxy, alkylsulfonyl, alkylmethyleneamino, phenylmethyleneamino or (substituted phenyl)methyleneamino;

R$_1$ is an acyl group derived from a carboxylic acid;

R$_2$ is hydrogen or methoxy;

R$_3$ and R$_4$ are the same or different and each is hydrogen, alkyl, cycloalkyl, phenyl or substituted phenyl, or one of R$_3$ and R$_4$ is hydrogen and the other is alkoxycarbonyl, alken-1-yl, alkyn-1-yl, 2-phenylethenyl, 2-phenylethynyl, carboxyl, —CH$_2$X$_1$ (wherein X$_1$ is azido, amino, hydroxy, alkanoylamino, alkylsulfonyloxy, phenylsulfonyloxy, (substituted phenyl)sulfonyloxy, phenyl, substituted phenyl, halogen, benzylthio, (substituted phenyl)methylthio, triphenylmethylthio, cyano or mercapto), —S—X$_2$ or —O—X$_2$ (wherein X$_2$ is alkyl, phenyl, substituted phenyl, alkanoyl, phenylcarbonyl, (substituted phenyl)carbonyl, or heteroarylcarbonyl), or $$-S-\underset{X_5}{\overset{X_3}{C}}-X_4 \quad \text{or} \quad -O-\underset{X_5}{\overset{X_3}{C}}-X_4$$

(Wherein one of X$_3$ and X$_4$ is hydrogen and the other is hydrogen or alkyl, or X$_3$ and X$_4$ when taken together with the carbon atom to which they are attached form a cycloalkyl group, and X$_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)-carbonyl, or cyano); and Z is oxygen or sulfur;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", "alkynyl", "alkyn-1-yl" and "alken-1-yl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 cabon atoms or carboxyl groups;

the term "substituted alkyl" refers to alkyl groups substituted with one or more azido, amino, alkylamino, dialkylamino, (phenylalkyl)amino, (substituted phenylalkyl)-amino, alkanoylamino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, tr iazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted slkyl, wherein the alkyl group has 1 to 4 carbon atoms, groups;

the term "a 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, piperidinyl, piperazinyl, imidazolylidinyl, oxazolylidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylimino, benzylimino or substituted alkyl, wherein the alkyl group has 1 to 4 carbon atoms, groups;

the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino.

2. A compound in accordance with claim 1 wherein Z is oxygen and $R_2$ is hydrogen.

3. A compound in accordance with claim 1 wherein Z is oxygen and $R_2$, $R_3$ and $R_4$ are each hydrogen.

4. A compound in accordance with claim 2 wherein $R_1$ is

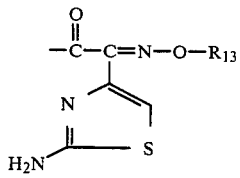

and $R_{13}$ is methyl, ethyl, carboxymethyl, 1-carboxy-1-methylethyl or 2,2,2-trifluoroethyl.

5. A compound in accordance with claim 2 wherein $R_1$ is

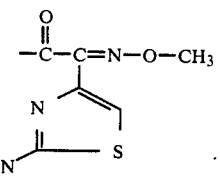

6. A compound in accordance with claim 2 wherein $R_1$ is

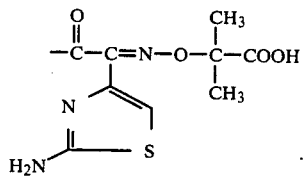

7. A compound in accordance with claim 2 wherein R is $NH_2$.

8. A compound in accordance with claim 2 wherein R is a 5, 6 or 7-membered heterocycle.

9. A compound in accordance with claim 2 wherein R is a 2,3-dioxo-1-piperazinyl, 4-alkyl-2,3-dioxo-1-piperazinyl or 4-phenyl-2,3-dioxo-1-piperazinyl.

10. A compound in accordance with claim 2 wherein R is 4-ethyl-2,3-dioxo-1-piperazinyl.

11. A compound in accordance with claim 2 wherein R is 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl-2-oxo-1-imidazolidinyl, 3-(substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl) amino]-2-oxo-1-imidazolidinyl or 3-[2-[(alkoxycarbonyl) amino]ethyl]-2-oxo-1-imidazolidinyl.

12. A compound in accordance with claim 2 wherein $R_1$ is 2-oxo-1-imidazolidinyl.

13. A compound in accordance with claim 1 having the formula

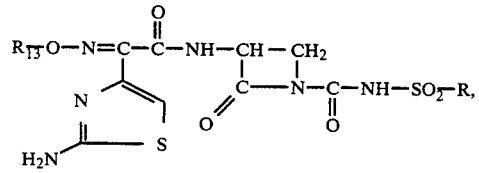

or a pharmaceutically acceptable salt thereof, wherein
$R_{13}$ is methyl, ethyl, carboxymethyl, 1-carboxy-1-methylethyl or 2,2,2-trifluoroethyl; and
R is $NH_2$, 2,3-dioxo-1-piperazinyl, 4-alkyl-2,3-dioxo-1-piperazinyl, 4-phenyl-2,3-dioxo-1-piperazinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imdazolidinyl, 3-phenyl-2-oxo-1-imidazolidinyl, 3-(substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl) amino]-2-oxo-1-imidazolidinyl or 3-[2-[(alkoxycarbonyl) amino]ethyl]-2-oxo-1-imidazolidinyl.

14. A compound in accordance with claim 13 wherein $R_{13}$ is methyl or 1-carboxy-1-methylethyl.

15. The compound in accordance with claim 1, [3S-[3α(Z), 4β]]-3-[[(2-amino-4-thiazolyl)(methoxyimino)acetyl]amino]-4-methyl-N-(methylsulfonyl)-2-oxo-1-azetidinecarboxamide, or a pharmaceutically acceptable salt thereof.

16. The compound in accordance with claim 1, [3S-[3α(Z),4β]]-3-[[(2-amino-4-thiazolyl)[(1-carboxy-1-methylethoxy)imino]acetyl]amino]-4-methyl-N-(methylsulfonyl)-2-oxo-1-azetidinecarboxamide, or a pharmaceutically acceptable salt thereof.

17. The compound in accordance with claim 1, [3S(Z)]-3-[[(2-amino-4-thiazolyl)(methoxyimino)acetyl]amino]-N-(methylsulfonyl)-2-oxo-1-azetidinecarbothioamide, or a pharmaceutically acceptable salt thereof.

18. The compound in accordance with claim 1, [3S(Z)]-2-[[[(1-(2-amino-4-thiazolyl)-2-[[1-[[(methylsulfonyl)amino]carbonyl]-2-oxo-3-azetidinyl]amino]-2-oxoethylidene]amino]oxy]-2-methylpropanoic acid, or a pharmaceutically acceptable salt thereof.

19. The compound in accordance with claim 1, azetidinecarboxamide, or a pharmaceutically acceptable salt thereof.

21. The compound in accordance with claim 1, [3S(Z)]-3-[[(2-amino-4-thiazolyl)(methoxyimino)acetyl]amino]-2-oxo-N-[(phenylamino)sulfonyl]-1-azetidinecarboxamide, or a pharmaceutically acceptable salt thereof.

22. The compound in accordance with claim 1, [3S(Z)]-3-[[(2-amino-4-thiazolyl)(methoxyimino)acetyl]amino]-N-[(dimethylamino)sulfonyl]-2-oxo-1-azetidinecarboxamide, or a pharmaceutically acceptable salt thereof.

23. The compound in accordance with claim 1, [3S(Z)]-2-[[[1-(2-amino-4-thiazolyl)-2-[[1-[[(aminosulfonyl)amino]carbonyl]-2-oxo-3-azetidinyl]amino]-2-oxoethylidene]amino]oxy]-2-methylpropanoic acid, or a pharmaceutically acceptable salt thereof.

24. The compound in accordance with claim 1,

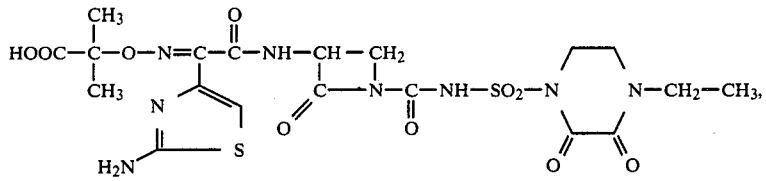

or a pharmaceutically acceptable salt thereof.

25. The compound in accordance with claim 1,

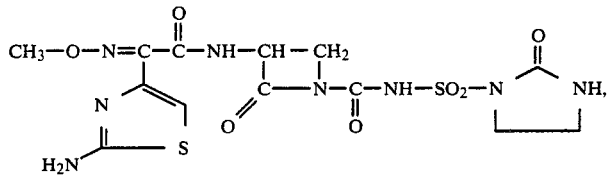

[3S(Z)]-3-[[(2-amino-4-thiazolyl)(methoxyimino)acetyl]amino]-N-(aminosulfonyl)-2-oxo-1-azetidinecarboxamide, or a pharmaceutically acceptable salt thereof.

26. The compound in accordance with claim 1,

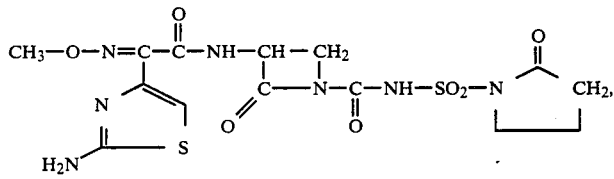

or a pharmaceutically acceptable salt thereof.

20. The compound in accordance with claim 1,

27. The compound in accordance with claim 1,

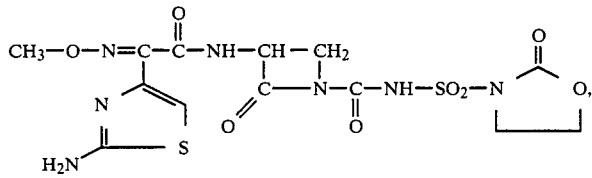

[3S(Z)]-3-[[(2-amino-4-thiazolyl)(methoxyimino)acetyl]amino]-N-[[(1-methylethyl)amino]sulfonyl]-2-oxo-1- or a pharmaceutically acceptable salt thereof.

28. The compound in accordance with claim 1,

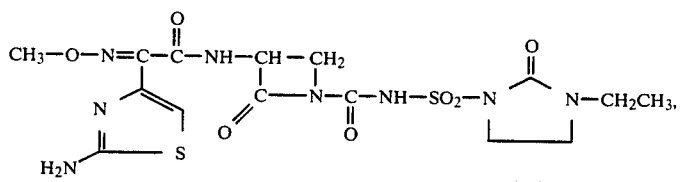

or a pharmaceutically acceptable salt thereof.

29. The compound in accordance with claim 1,

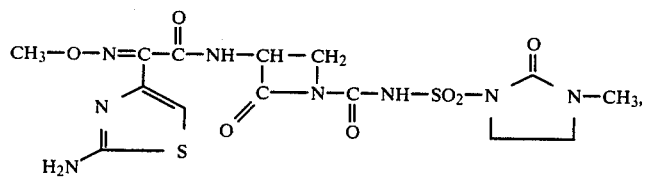

or a pharmaceutically acceptable salt thereof.

30. The compound in accordance with claim 1,

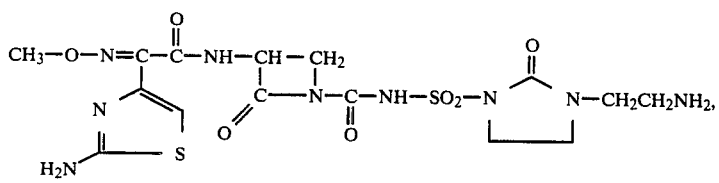

or a pharmaceutically acceptable salt thereof.

31. A β-lactam having the formula

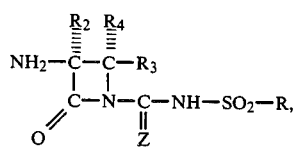

or a salt thereof; wherein

R is alkyl, alkenyl, alkynyl, substituted alkyl, phenyl, substituted phenyl, a 5, 6 or 7-membered heterocycle, phenylalkyl, (substituted phenyl)alkyl, (5, 6 or 7-membered heterocycle)alkyl, or —NR$_a$R$_b$ wherein R$_a$ and R$_b$ are the same or different and each is hydrogen, alkyl, substituted alkyl, phenyl, substituted phenyl, phenylalkyl, or (substituted phenyl)alkyl or one of R$_a$ and R$_b$ is hydrogen, alkyl, phenyl, substituted phenyl, phenylalkyl or (substituted phenyl)alkyl and the other is amino, alkanoylamino, arylcarbonylamino, alkoxycarbonylamino, alkylsulfonylamino, alkylamino, dialkylamino, phenylamino, (substituted phenyl)amino, hydroxy, cyano, alkoxy, phenyloxy, (substituted phenyl)oxy, phenylalkoxy, (substituted phenyl)alkoxy, a 5, 6 or 7-membered heterocycle, (5, 6 or 7-membered heterocycle)alkyl, (5, 6 or 7-membered heterocycle)alkoxy, alkylsulfonyl, alkylmethyleneamino, phenylmethyleneamino or (substituted phenyl)methyleneamino;

R$_2$ is hydrogen or methoxy;

R$_3$ and R$_4$ are the same or different and each is hydrogen, alkyl, cycloalkyl, phenyl or substituted phenyl, or one of R$_3$ and R$_4$ is hydrogen and the other is alkoxycarbonyl, alken-1-yl, alkyn-1-yl, 2-phenylethenyl, 2-phenylethynyl, carboxyl, —CH$_2$X$_1$ (wherein X$_1$ is azido, amino, hydroxy, alkanoylamino, alkylsulfonyloxy, phenylsulfonyloxy, (substituted phenyl)sulfonyloxy, phenyl, substituted phenyl, halogen, benzylthio, (substituted phenyl)methylthio, triphenylmethylthio, cyano or mercapto), —S—X$_2$ or —O—X$_2$ (wherein X$_2$ is alkyl, phenyl, substituted phenyl, alkanoyl, phenylcarbonyl, (substituted phenyl)carbonyl, or heteroarylcarbonyl), or

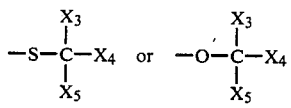

(wherein one of X$_3$ and X$_4$ is hydrogen and the other is hydrogen or alkyl, or X$_3$ and X$_4$ when taken together with the carbon atom to which they are attached form a cycloalkyl group, and X$_5$ is formyl, alkanoyl, phenylcarbonyl, (substituted phenyl)carbonyl, phenylalkylcarbonyl, (subtituted phenyl)alkylcarbonyl, carboxyl, alkoxycarbonyl, aminocarbonyl, (substituted amino)-carbonyl, or cyano); and Z is oxygen or sulfur;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", "alkynyl", "alkyn-1-yl" and "alken-1-yl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the term "substituted alkyl" refers to alkyl groups substituted with one or more azido, amino, alkylamino, dialkylamino, (phenylalkyl)amino, (substituted phenylalkyl)-amino, alkanoylamino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl or substituted alkyl, wherein the alkyl group has 1 to 4 carbon atoms, groups;

the term "a 5, 6 or 7-membered heterocycle" refers to pyridinyl, fuuranyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, piperidinyl, piperazinyl, imidazolylidinyl, oxazolylidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylimino, benzylimino or substituted alkyl, wherein the alkyl group has 1 to 4 carbon atoms, groups;

the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino.

32. A compound in accordance with claim 31 wherein Z is oxygen and $R_2$ is hydrogen.

33. a compound in accordance with claim 31 wherein Z is oxygen and $R_2$, $R_3$ and $R_4$ are each hydrogen.

34. A compound in accordance with claim 31 having the formula

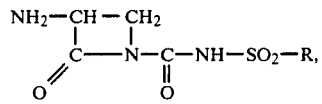

or a salt thereof; wherein

R is NH$_2$, 2,3-dioxo-1-piperazinyl, 4-alkyl-2,3-dioxo-1-piperazinyl, 4-phenyl-2,3-dioxo-1-piperazinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl-2-oxo-1-imidazolidinyl, 3-(substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl) amino]-2-oxo-1-imidazolidinyl or 3-[2-[(alkoxycarbonyl) amino]ethyl]-2-oxo-1-imidazolidinyl.

35. The compound in accordance with claim 31, (S)-N-(methylsulfonyl)-2-oxo-3-amino-1azetidinecarboxamide, or a salt thereof.

36. The compound in accordance with claim 31, (S)-3-amino-N-(methylsulfonyl)-2-oxo-1-azetidinecarboxamide, or a salt thereof.

37. The compound in accordance with claim 31, [3S-[3α,4β]]-3-amino-4-methyl-N-(methylsulfonyl)-2-oxo-1-azetidinecarboxamide, or a salt thereof.

38. The compound in accordance with claim 31, (S)-3-amino-N-(methylsulfonyl)-2-oxo-1-azetidinecarbothioamide, or a salt thereof.

39. The compound in accordance with claim 31, (S)-3-amino-N-(aminosulfonyl)-2-oxo-1-azetidinecarboxamide, or a salt thereof.

40. The compound in accordance with claim 31, (S)-3-amino-N-[(methylamino)sulfonyl]-2-oxo-1-azetidinecarboxamide, or a salt thereof.

41. The compound in accordance with claim 31, (S)-3-amino-2-oxo-N-[[(4-pyridyl)amino]sulfonyl]-1-azetidinecarboxamide, or a salt thereof.

42. The compound in accordance with claim 31, (S)-1-[[[(4-methylphenyl)sulfonyl]amino]carbonyl]-2-oxo-3-aminoazetidine, or a salt thereof.

* * * * *

UNITED STATES PATENT AND TRADEMARK OFFICE
CERTIFICATE OF CORRECTION

PATENT NO. : 4,587,047
DATED : May 6, 1986
INVENTOR(S) : Hermann Breuer et al.

It is certified that error appears in the above-identified patent and that said Letters Patent is hereby corrected as shown below:

Column 14, formula V, add a bond "≡" under "$R_4$".

Column 14, formula VI, add a bond "≡" under "$R_4$".

Column 28, line 56, "solutions" should be --solution--.

Column 30, line 26, "1%" should be --10%--.

Column 37, line 42, add a left parenthesis "(" before "8.5 g".

Column 38, lines 6 and 7, "methyodyimino" should be --methoxyimino--.

UNITED STATES PATENT AND TRADEMARK OFFICE
CERTIFICATE OF CORRECTION

PATENT NO. : 4,587,047

DATED : May 6, 1986

INVENTOR(S) : Hermann Breuer et al.

It is certified that error appears in the above-identified patent and that said Letters Patent is hereby corrected as shown below:

Column 38, line 18, "dimethyldormamide" should be --dimethylformamide--.

Column 40, line 22, add --255-- after "250°-".

Column 42, title of Example 35, add -- 4- -- after "(2-Amino-".

Column 46, line 36, replace "60" after "(2-amino-" with --$\alpha$--.

Column 65, line 25, "slkyl" should be --alkyl--.

Signed and Sealed this

Twenty-first Day of October, 1986

[SEAL]

Attest:

DONALD J. QUIGG

Attesting Officer     Commissioner of Patents and Trademarks